(12) United States Patent
Anderson et al.

(10) Patent No.: US 11,918,468 B2
(45) Date of Patent: Mar. 5, 2024

(54) TRANSVERSE HELICAL CARDIAC ANCHOR FOR MINIMALLY INVASIVE HEART VALVE REPAIR

(71) Applicant: NeoChord, Inc., St. Louis Park, MN (US)

(72) Inventors: Edward J. Anderson, Maple Grove, MN (US); Randall Beyreis, Corcoran, MN (US); Brady Hatcher, Rogers, MN (US); Tyler Nordmann, Maple Grove, MN (US); Daryl Edmiston, Draper, UT (US)

(73) Assignee: NeoChord, Inc., Maple Grove, MN (US)

( * ) Notice: Subject to any disclaimer, the term of this patent is extended or adjusted under 35 U.S.C. 154(b) by 0 days.

(21) Appl. No.: 17/845,490

(22) Filed: Jun. 21, 2022

(65) Prior Publication Data

US 2022/0313437 A1 Oct. 6, 2022

Related U.S. Application Data

(63) Continuation of application No. 16/850,827, filed on Apr. 16, 2020, now Pat. No. 11,376,126.
(Continued)

(51) Int. Cl.
*A61F 2/24* (2006.01)

(52) U.S. Cl.
CPC .......... *A61F 2/2457* (2013.01); *A61F 2/2466* (2013.01); *A61F 2220/0008* (2013.01);
(Continued)

(58) Field of Classification Search
CPC .............. A61F 2230/0091; A61F 2/246; A61F 2/2466; A61F 2/2457; A61F 2/2454; A61F 2/2445; A61F 2220/0016; A61F 2/2427; A61F 2220/0008; A61F 2220/0075; A61F 2/243; A61F 2250/001; A61F 2/24; A61F 2002/9511; A61B 17/0401; A61B 2017/00243; A61B 2017/0496;
(Continued)

(56) References Cited

U.S. PATENT DOCUMENTS 2,751,908 A 6/1956 Wallace
3,664,330 A 5/1972 Deutsch
(Continued)

FOREIGN PATENT DOCUMENTS

EP 1039851 B1 7/2005
EP 1637091 A2 3/2006
(Continued)

OTHER PUBLICATIONS

Interactive Cardio Vascular and Thoracic Surgery; Abstracts; Suppl 3 to vol. 7 (Sep. 2008) 52 pages.
(Continued)

*Primary Examiner* — Seema Mathew
(74) *Attorney, Agent, or Firm* — Merchant & Gould P.C.

(57) ABSTRACT

Disclosed herein are various embodiments of cardiac anchors configured to be inserted into a heart wall of a patient to anchor a suture as an artificial chordae under an appropriate tension for proper valve function. Such cardiac anchors are particularly suitable for use in intravascular, transcatheter procedures.

20 Claims, 26 Drawing Sheets

Related U.S. Application Data

(60) Provisional application No. 62/834,512, filed on Apr. 16, 2019.

(52) U.S. Cl.
CPC .............. *A61F 2220/0016* (2013.01); *A61F 2230/0071* (2013.01); *A61F 2230/0091* (2013.01)

(58) Field of Classification Search
CPC .. A61B 2017/0414; A61B 2017/00783; A61B 17/0487; A61B 17/00234; A61B 2017/0488; A61B 2017/048; A61B 17/0485; A61B 2017/047; A61B 2017/06052; A61B 2017/06076; A61B 2017/06176
See application file for complete search history.

(56) References Cited

U.S. PATENT DOCUMENTS

| | | |
|---|---|---|
| 3,667,474 A | 6/1972 | Lapkin |
| 3,842,840 A | 10/1974 | Schweizer |
| 4,258,716 A | 3/1981 | Sutherland |
| 4,351,345 A | 9/1982 | Carney |
| 4,759,348 A | 7/1988 | Cawood |
| 4,836,204 A | 6/1989 | Landymore et al. |
| 4,935,027 A | 6/1990 | Yoon |
| 4,957,498 A | 9/1990 | Caspari et al. |
| 4,967,498 A | 9/1990 | Caspari |
| 4,960,424 A | 10/1990 | Grooters |
| 4,967,798 A | 11/1990 | Hammer |
| 4,972,874 A | 11/1990 | Jackson |
| 5,053,013 A | 10/1991 | Ensminger |
| 5,059,201 A | 10/1991 | Asnis |
| 5,211,650 A | 5/1993 | Noda |
| 5,297,536 A | 3/1994 | Wilk |
| 5,304,185 A | 4/1994 | Taylor |
| 5,312,423 A | 5/1994 | Rosenbluth et al. |
| 5,336,229 A | 8/1994 | Noda |
| 5,350,397 A * | 9/1994 | Palermo ............. A61B 18/1492 606/191 |
| 5,383,877 A | 1/1995 | Clarke |
| 5,431,666 A | 7/1995 | Sauer et al. |
| 5,452,733 A | 9/1995 | Sterman |
| 5,474,519 A | 12/1995 | Bloomer |
| 5,547,455 A | 8/1996 | McKenna et al. |
| 5,556,411 A | 9/1996 | Taoda et al. |
| 5,571,215 A | 11/1996 | Sterman |
| 5,601,578 A | 2/1997 | Murphy |
| 5,626,607 A | 5/1997 | Malecki |
| 5,653,716 A | 8/1997 | Malo et al. |
| 5,665,100 A | 9/1997 | Yoon |
| 5,667,472 A | 9/1997 | Finn et al. |
| 5,667,473 A | 9/1997 | Finn et al. |
| 5,667,478 A | 9/1997 | McFarlin et al. |
| 5,693,091 A | 12/1997 | Larson, Jr. et al. |
| 5,728,113 A | 3/1998 | Sherts |
| 5,762,458 A | 6/1998 | Wang et al. |
| 5,762,613 A | 6/1998 | Sutton et al. |
| 5,766,163 A | 6/1998 | Mueller et al. |
| 5,769,791 A | 6/1998 | Benaron et al. |
| 5,772,597 A | 6/1998 | Goldberger et al. |
| 5,772,672 A | 6/1998 | Toy et al. |
| 5,785,658 A | 7/1998 | Benaron et al. |
| 5,797,960 A | 8/1998 | Stevens et al. |
| 5,830,231 A | 11/1998 | Geiges, Jr. |
| 5,839,639 A | 11/1998 | Sauer et al. |
| 5,857,961 A | 1/1999 | Vanden Hoek et al. |
| 5,897,564 A | 4/1999 | Schulze et al. |
| 5,908,428 A | 6/1999 | Scirica et al. |
| 5,908,429 A | 6/1999 | Yoon |
| 5,919,128 A | 7/1999 | Fitch |
| 5,961,440 A | 10/1999 | Schweich, Jr |
| 5,972,004 A | 10/1999 | Williamson et al. |
| 5,972,030 A | 10/1999 | Garrison et al. |
| 5,984,939 A | 11/1999 | Yoon |
| 5,993,466 A | 11/1999 | Yoon |
| 5,993,467 A | 11/1999 | Yoon |
| 6,022,360 A | 2/2000 | Reimels et al. |
| 6,045,497 A | 4/2000 | Schweich, Jr |
| 6,050,936 A | 4/2000 | Schweich, Jr |
| 6,053,933 A | 4/2000 | Balazs et al. |
| 6,059,715 A | 5/2000 | Schweich, Jr |
| 6,077,214 A | 6/2000 | Mortier et al. |
| 6,093,199 A * | 7/2000 | Brown ............. A61B 17/12118 606/200 |
| 6,117,144 A | 9/2000 | Nobles et al. |
| 6,129,683 A | 10/2000 | Sutton et al. |
| 6,149,660 A | 11/2000 | Laufer et al. |
| 6,152,934 A | 11/2000 | Harper et al. |
| 6,162,168 A | 12/2000 | Schweich, Jr |
| 6,162,233 A | 12/2000 | Williamson |
| 6,162,234 A | 12/2000 | Freedland |
| 6,165,119 A | 12/2000 | Schweich, Jr |
| 6,165,120 A | 12/2000 | Schweich, Jr |
| 6,165,183 A | 12/2000 | Kuehn et al. |
| 6,178,346 B1 | 1/2001 | Amundson et al. |
| 6,179,195 B1 | 1/2001 | Adams et al. |
| 6,183,411 B1 | 2/2001 | Mortier et al. |
| 6,190,357 B1 | 2/2001 | Ferrari et al. |
| 6,234,079 B1 | 5/2001 | Chertkow |
| 6,234,995 B1 | 5/2001 | Peacock, III |
| 6,245,079 B1 | 6/2001 | Nobles et al. |
| 6,260,552 B1 | 7/2001 | Mortier et al. |
| 6,261,222 B1 | 7/2001 | Schweich, Jr |
| 6,264,602 B1 | 7/2001 | Mortier et al. |
| 6,269,819 B1 | 8/2001 | Oz et al. |
| 6,270,508 B1 | 8/2001 | Klleman et al. |
| 6,283,993 B1 | 9/2001 | Cosgrove et al. |
| 6,312,447 B1 | 11/2001 | Grimes |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,355,050 B1 | 3/2002 | Andreas et al. |
| 6,401,720 B1 | 6/2002 | Stevens et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,419,626 B1 | 7/2002 | Yoon |
| 6,436,107 B1 | 8/2002 | Wang et al. |
| 6,443,922 B1 | 9/2002 | Roberts et al. |
| 6,451,054 B1 | 9/2002 | Stevens |
| 6,461,366 B1 | 10/2002 | Seguin |
| 6,508,777 B1 | 1/2003 | Macoviak et al. |
| 6,514,194 B2 | 2/2003 | Schweich, Jr. et al. |
| 6,533,796 B1 | 3/2003 | Sauer et al. |
| 6,537,198 B1 | 3/2003 | Vidlund et al. |
| 6,537,314 B2 | 3/2003 | Langberg et al. |
| 6,551,331 B2 | 4/2003 | Nobles et al. |
| 6,558,416 B2 | 5/2003 | Cosgrove et al. |
| 6,562,052 B2 | 5/2003 | Nobles et al. |
| 6,564,805 B2 | 5/2003 | Garrison et al. |
| 6,582,388 B1 | 6/2003 | Coleman et al. |
| 6,585,727 B1 | 7/2003 | Cashman et al. |
| 6,589,160 B2 | 7/2003 | Schweich, Jr. et al. |
| 6,602,288 B1 | 8/2003 | Cosgrove et al. |
| 6,616,684 B1 | 9/2003 | Vidlund et al. |
| 6,619,291 B2 | 9/2003 | Hlavka et al. |
| 6,622,730 B2 | 9/2003 | Ekvall et al. |
| 6,626,917 B1 | 9/2003 | Craig |
| 6,626,930 B1 | 9/2003 | Allen et al. |
| 6,629,534 B1 | 10/2003 | Goar et al. |
| 6,629,921 B1 | 10/2003 | Schweich, Jr. et al. |
| 6,629,984 B1 | 10/2003 | Chan |
| 6,645,205 B2 | 11/2003 | Ginn |
| 6,679,268 B2 | 1/2004 | Stevens et al. |
| 6,692,605 B2 | 2/2004 | Kerr et al. |
| 6,695,866 B1 | 2/2004 | Kuehn et al. |
| 6,709,456 B2 | 3/2004 | Langberg et al. |
| 6,718,985 B2 | 4/2004 | Hlavka et al. |
| 6,723,038 B1 | 4/2004 | Schroeder et al. |

(56) References Cited

U.S. PATENT DOCUMENTS

| | | |
|---|---|---|
| 6,733,509 B2 | 5/2004 | Nobles et al. |
| 6,740,107 B2 | 5/2004 | Loeb et al. |
| 6,743,239 B1 | 6/2004 | Kuehn et al. |
| 6,746,471 B2 | 6/2004 | Mortier et al. |
| 6,752,713 B2 | 6/2004 | Johnson, Jr. |
| 6,752,813 B2 | 6/2004 | Goldfarb et al. |
| 6,755,777 B2 | 6/2004 | Schweich, Jr. et al. |
| 6,764,510 B2 | 7/2004 | Vidlund et al. |
| 6,770,083 B2 | 8/2004 | Seguin |
| 6,770,084 B1 | 8/2004 | Bain et al. |
| 6,793,618 B2 | 9/2004 | Schweich, Jr. et al. |
| 6,802,860 B2 | 10/2004 | Cosgrove et al. |
| 6,808,488 B2 | 10/2004 | Mortier et al. |
| 6,810,882 B2 | 11/2004 | Langberg et al. |
| 6,840,246 B2 | 1/2005 | Downing |
| 6,858,003 B2 | 2/2005 | Evans et al. |
| 6,875,224 B2 | 4/2005 | Grimes |
| 6,893,448 B2 | 5/2005 | O'Quinn et al. |
| 6,896,686 B2 | 5/2005 | Weber |
| 6,908,424 B2 | 6/2005 | Mortier et al. |
| 6,918,917 B1 | 7/2005 | Nguyen et al. |
| 6,921,407 B2 | 7/2005 | Nguyen et al. |
| 6,929,715 B2 | 8/2005 | Fladda et al. |
| 6,936,054 B2 | 8/2005 | Chu |
| 6,955,175 B2 | 10/2005 | Stevens et al. |
| 6,962,605 B2 | 11/2005 | Cosgrove et al. |
| 6,978,176 B2 | 12/2005 | Lattouf |
| 6,986,775 B2 | 1/2006 | Morales et al. |
| 6,989,028 B2 | 1/2006 | Lashinski et al. |
| 6,991,635 B2 | 1/2006 | Takamoto et al. |
| 6,997,950 B2 | 2/2006 | Chawla |
| 7,004,176 B2 | 2/2006 | Lau |
| 7,004,952 B2 | 2/2006 | Nobles et al. |
| 7,011,669 B2 | 3/2006 | Kimblad |
| 7,044,905 B2 | 5/2006 | Vidlund et al. |
| 7,048,754 B2 | 5/2006 | Martin et al. |
| 7,077,862 B2 | 7/2006 | Vidlund et al. |
| 7,083,628 B2 | 8/2006 | Bachman |
| 7,083,638 B2 | 8/2006 | Foerster |
| 7,090,686 B2 | 8/2006 | Nobles et al. |
| 7,094,244 B2 | 8/2006 | Schreck |
| 7,100,614 B2 | 9/2006 | Stevens et al. |
| 7,112,207 B2 | 9/2006 | Allen et al. |
| 7,112,219 B2 | 9/2006 | Vidlund et al. |
| 7,115,110 B2 | 10/2006 | Frazier et al. |
| 7,118,583 B2 | 10/2006 | O'Quinn et al. |
| 7,122,040 B2 | 10/2006 | Hill et al. |
| 7,179,291 B2 | 2/2007 | Rourke et al. |
| 7,186,264 B2 | 3/2007 | Liddicoat et al. |
| 7,189,199 B2 | 3/2007 | McCarthy et al. |
| 7,217,240 B2 | 5/2007 | Snow |
| 7,226,467 B2 | 6/2007 | Lucatero et al. |
| 7,247,134 B2 | 7/2007 | Vidlund et al. |
| 7,250,028 B2 | 7/2007 | Julian et al. |
| 7,288,097 B2 | 10/2007 | Seguin |
| 7,294,148 B2 | 11/2007 | McCarthy |
| 7,381,210 B2 | 6/2008 | Zarbatany et al. |
| 7,464,712 B2 | 12/2008 | Oz et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,386 B1 | 12/2009 | Gammie |
| 7,666,204 B2 | 2/2010 | Thornton et al. |
| 7,815,654 B2 | 10/2010 | Chu |
| 7,879,048 B2 | 2/2011 | Bain et al. |
| 7,887,552 B2 | 2/2011 | Bachman |
| 7,959,679 B2* | 6/2011 | Lambrecht ............ A61B 5/1076 |
| | | 623/17.11 |
| 8,012,151 B1* | 9/2011 | Laufer ............... A61B 18/1492 |
| | | 606/41 |
| 8,303,622 B2 | 11/2012 | Alkhatib |
| 8,465,500 B2 | 6/2013 | Speziali |
| 8,512,362 B2 | 8/2013 | Ewers et al. |
| 8,545,551 B2 | 10/2013 | Loulmet |
| 8,728,097 B1* | 5/2014 | Sugimoto ............ A61B 17/068 |
| | | 606/142 |
| 8,758,393 B2 | 6/2014 | Zentgraf |
| 8,771,296 B2 | 7/2014 | Nobles et al. |
| 8,938,283 B2 | 1/2015 | Zentgraf et al. |
| 8,968,338 B2 | 3/2015 | Speziali |
| 9,044,221 B2 | 6/2015 | Zentgraf et al. |
| 9,192,374 B2 | 11/2015 | Zentgraf |
| 9,364,213 B2 | 6/2016 | Speziali |
| 9,393,080 B2 | 7/2016 | Zentgraf et al. |
| 9,517,337 B2* | 12/2016 | Ollivier ............... A61N 1/3756 |
| 9,668,860 B2 | 6/2017 | Kudlik et al. |
| 9,700,300 B2 | 7/2017 | Speziali |
| 9,877,833 B1* | 1/2018 | Bishop .................. A61F 2/2457 |
| 10,022,114 B2* | 7/2018 | Gilmore ............ A61B 17/0487 |
| 10,058,321 B2 | 8/2018 | Sampson |
| 10,058,323 B2* | 8/2018 | Maisano ............ A61B 17/0487 |
| 10,065,032 B2 | 9/2018 | Ollivier |
| 10,080,659 B1 | 9/2018 | Zentgraf et al. |
| 10,112,045 B2 | 10/2018 | Anderson |
| 10,130,474 B2 | 11/2018 | Zentgraf et al. |
| 10,213,306 B2 | 2/2019 | Colli |
| 10,314,586 B2 | 6/2019 | Greenberg et al. |
| 10,327,743 B2 | 6/2019 | St. Goar et al. |
| 10,328,272 B2 | 6/2019 | Delanely, Jr |
| 10,391,306 B2 | 8/2019 | Ma |
| 10,420,645 B2 | 9/2019 | Del Nido |
| 10,478,302 B2* | 11/2019 | Seguin ................. A61F 2/2427 |
| 10,499,941 B2 | 12/2019 | Suri |
| 10,507,018 B2 | 12/2019 | Zentgraf |
| 10,548,733 B2 | 2/2020 | Purcell |
| 10,582,924 B2 | 3/2020 | Speziali |
| 10,588,620 B2 | 3/2020 | Caffes et al. |
| 10,653,524 B2 | 5/2020 | Khairkhahan |
| 10,695,178 B2 | 6/2020 | Zengraf et al. |
| 10,709,433 B2 | 7/2020 | Flanagan |
| 10,765,715 B2 | 9/2020 | Kang et al. |
| 10,856,987 B2 | 12/2020 | Cabiri |
| 10,925,731 B2 | 2/2021 | Bishop |
| 11,160,655 B2* | 11/2021 | Keane ................. A61F 2/2454 |
| 11,413,146 B2* | 8/2022 | Rabito .................. A61F 2/2442 |
| 2001/0005787 A1 | 6/2001 | Oz |
| 2001/0016675 A1 | 8/2001 | Mortier et al. |
| 2001/0021872 A1 | 9/2001 | Bailey et al. |
| 2002/0013571 A1 | 1/2002 | Goldfarb et al. |
| 2002/0020732 A1 | 2/2002 | Adams et al. |
| 2002/0029080 A1 | 3/2002 | Mortier et al. |
| 2002/0049402 A1 | 4/2002 | Peacock, III |
| 2002/0077524 A1 | 6/2002 | Schweich, Jr |
| 2002/0091382 A1 | 7/2002 | Hooven |
| 2002/0169359 A1 | 11/2002 | McCarthy |
| 2002/0173694 A1 | 11/2002 | Mortier et al. |
| 2002/0183766 A1 | 12/2002 | Seguin |
| 2002/0183787 A1 | 12/2002 | Wahr et al. |
| 2003/0004562 A1 | 1/2003 | DiCarlo |
| 2003/0032979 A1 | 2/2003 | Mortier et al. |
| 2003/0050529 A1 | 3/2003 | Vidlund et al. |
| 2003/0050693 A1 | 3/2003 | Quijano |
| 2003/0078599 A1 | 4/2003 | O'Quinn et al. |
| 2003/0078600 A1 | 4/2003 | O'Quinn et al. |
| 2003/0105519 A1 | 6/2003 | Fasol |
| 2003/0120341 A1 | 6/2003 | Shennib et al. |
| 2003/0130731 A1 | 7/2003 | Vidlund et al. |
| 2003/0163029 A1 | 8/2003 | Sonnenschein et al. |
| 2003/0166992 A1 | 9/2003 | Schweich, Jr |
| 2003/0167071 A1 | 9/2003 | Martin et al. |
| 2003/0171641 A1 | 9/2003 | Schweich, Jr |
| 2003/0181928 A1 | 9/2003 | Vidlund et al. |
| 2003/0187457 A1 | 10/2003 | Weber |
| 2003/0195529 A1 | 10/2003 | Takamoto et al. |
| 2003/0199975 A1 | 10/2003 | Gabbay |
| 2004/0003819 A1 | 1/2004 | St. Goar |
| 2004/0030382 A1 | 2/2004 | St. Goar |
| 2004/0039442 A1 | 2/2004 | St. Goar |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049552 A1 | 3/2004 | Motoyama |
| 2004/0087975 A1 | 5/2004 | Lucatero et al. |

(56) References Cited

U.S. PATENT DOCUMENTS

| | | |
|---|---|---|
| 2004/0087978 A1 | 5/2004 | Velez et al. |
| 2004/0092962 A1 | 5/2004 | Thornton et al. |
| 2004/0093023 A1 | 5/2004 | Allen et al. |
| 2004/0097805 A1 | 5/2004 | Verard et al. |
| 2004/0116767 A1 | 6/2004 | Lebovic |
| 2004/0122448 A1 | 6/2004 | Levine |
| 2004/0127983 A1 | 7/2004 | Mortier et al. |
| 2004/0133063 A1 | 7/2004 | McCarthy et al. |
| 2004/0167374 A1 | 8/2004 | Schweich et al. |
| 2004/0167539 A1 | 8/2004 | Kuehn et al. |
| 2004/0220593 A1 | 11/2004 | Grennhalgh |
| 2004/0225300 A1 | 11/2004 | Goldfarb et al. |
| 2004/0225304 A1 | 11/2004 | Vidlund et al. |
| 2004/0236353 A1 | 11/2004 | Bain et al. |
| 2004/0236354 A1 | 11/2004 | Seguin |
| 2004/0236373 A1 | 11/2004 | Anspach, III |
| 2004/0243229 A1 | 12/2004 | Vidlund et al. |
| 2004/0249367 A1 | 12/2004 | Saadat |
| 2004/0267083 A1 | 12/2004 | McCarthy |
| 2005/0004668 A1 | 1/2005 | Aklog et al. |
| 2005/0021055 A1 | 1/2005 | Toubia et al. |
| 2005/0021056 A1 | 1/2005 | St. Goar |
| 2005/0021057 A1 | 1/2005 | St. Goar |
| 2005/0033446 A1 | 2/2005 | Deem et al. |
| 2005/0044365 A1 | 2/2005 | Bachman |
| 2005/0065396 A1 | 3/2005 | Mortier et al. |
| 2005/0075723 A1 | 4/2005 | Schroeder et al. |
| 2005/0075727 A1 | 4/2005 | Wheatley |
| 2005/0101975 A1 | 5/2005 | Nguyen et al. |
| 2005/0125011 A1 | 6/2005 | Spence et al. |
| 2005/0131277 A1 | 6/2005 | Schweich |
| 2005/0131533 A1 | 6/2005 | Alfieri et al. |
| 2005/0143620 A1 | 6/2005 | Mortier et al. |
| 2005/0148815 A1 | 7/2005 | Mortier et al. |
| 2005/0149014 A1 | 7/2005 | Hauck et al. |
| 2005/0154402 A1 | 7/2005 | Sauer et al. |
| 2005/0165419 A1 | 7/2005 | Sauer et al. |
| 2005/0171601 A1 | 8/2005 | Cosgrove |
| 2005/0216039 A1 | 9/2005 | Lederman |
| 2005/0240202 A1 | 10/2005 | Shennib et al. |
| 2005/0245932 A1* | 11/2005 | Fanton ............... A61B 17/0401 606/232 |
| 2005/0250987 A1 | 11/2005 | Ewers |
| 2005/0251187 A1 | 11/2005 | Beane et al. |
| 2005/0251201 A1 | 11/2005 | Roue |
| 2006/0020275 A1 | 1/2006 | Goldfarb et al. |
| 2006/0036317 A1 | 2/2006 | Vidlund et al. |
| 2006/0041306 A1 | 2/2006 | Vidlund et al. |
| 2006/0052868 A1 | 3/2006 | Mortier et al. |
| 2006/0058871 A1 | 3/2006 | Zakay et al. |
| 2006/0074484 A1 | 4/2006 | Huber |
| 2006/0074485 A1 | 4/2006 | Realyvasquez |
| 2006/0089671 A1 | 4/2006 | Goldfarb et al. |
| 2006/0100699 A1 | 5/2006 | Vidlund et al. |
| 2006/0106405 A1* | 5/2006 | Fann ....................... A61B 17/11 606/142 |
| 2006/0127509 A1 | 6/2006 | Eckman |
| 2006/0135993 A1 | 6/2006 | Seguin |
| 2006/0149123 A1 | 7/2006 | Vidlund et al. |
| 2006/0161040 A1 | 7/2006 | McCarthy |
| 2006/0161193 A1 | 7/2006 | Beane et al. |
| 2006/0184203 A1 | 8/2006 | Martin et al. |
| 2006/0195012 A1 | 8/2006 | Mortier et al. |
| 2006/0195134 A1 | 8/2006 | Crittenden |
| 2006/0195183 A1 | 8/2006 | Navia et al. |
| 2006/0212071 A1 | 9/2006 | Ginn |
| 2006/0241340 A1 | 10/2006 | Vidlund |
| 2006/0287657 A1 | 12/2006 | Bachman |
| 2007/0002627 A1 | 1/2007 | Youn |
| 2007/0027451 A1 | 2/2007 | Desinger et al. |
| 2007/0038293 A1 | 2/2007 | St.Goar et al. |
| 2007/0049952 A1 | 3/2007 | Weiss |
| 2007/0050022 A1 | 3/2007 | Vidlund et al. |
| 2007/0055303 A1 | 3/2007 | Vidlund et al. |
| 2007/0088375 A1 | 4/2007 | Beane et al. |
| 2007/0100356 A1 | 5/2007 | Lucatero et al. |
| 2007/0112244 A1 | 5/2007 | McCarthy |
| 2007/0112425 A1* | 5/2007 | Schaller ............. A61B 17/0469 606/135 |
| 2007/0118151 A1 | 5/2007 | Davidson |
| 2007/0118154 A1 | 5/2007 | Crabtree |
| 2007/0118155 A1 | 5/2007 | Goldfarb et al. |
| 2007/0118213 A1 | 5/2007 | Loulmet |
| 2007/0129737 A1 | 6/2007 | Goldfarb et al. |
| 2007/0179511 A1 | 8/2007 | Paolitto |
| 2007/0197858 A1 | 8/2007 | Goldfarb et al. |
| 2007/0203391 A1 | 8/2007 | Bloom et al. |
| 2007/0232941 A1 | 10/2007 | Rabinovich |
| 2007/0239272 A1 | 10/2007 | Navia et al. |
| 2007/0265643 A1 | 11/2007 | Beane et al. |
| 2007/0299468 A1 | 12/2007 | Viola |
| 2008/0004485 A1 | 1/2008 | Moreschi |
| 2008/0027468 A1 | 1/2008 | Fenton et al. |
| 2008/0051703 A1 | 2/2008 | Thornton et al. |
| 2008/0051807 A1* | 2/2008 | St. Goar ............. A61B 17/0625 606/232 |
| 2008/0065011 A1 | 3/2008 | Marchand et al. |
| 2008/0065156 A1 | 3/2008 | Hauser et al. |
| 2008/0065205 A1 | 3/2008 | Nguyen et al. |
| 2008/0091059 A1 | 4/2008 | Machold |
| 2008/0091264 A1 | 4/2008 | Machold |
| 2008/0097482 A1 | 4/2008 | Bain et al. |
| 2008/0097489 A1 | 4/2008 | Goldfarb et al. |
| 2008/0109069 A1 | 5/2008 | Coleman et al. |
| 2008/0125860 A1 | 5/2008 | Webler |
| 2008/0125861 A1 | 5/2008 | Webler et al. |
| 2008/0167714 A1 | 7/2008 | St. Goar |
| 2008/0183194 A1 | 7/2008 | Goldfarb et al. |
| 2008/0188873 A1 | 8/2008 | Speziali |
| 2008/0195126 A1 | 8/2008 | Solem |
| 2008/0195200 A1 | 8/2008 | Vidlund et al. |
| 2008/0208006 A1 | 8/2008 | Farr |
| 2008/0228223 A1 | 9/2008 | Alkhatib |
| 2008/0243245 A1 | 10/2008 | Thamber et al. |
| 2009/0062819 A1 | 3/2009 | Burkhart et al. |
| 2009/0093670 A1 | 4/2009 | Annest |
| 2009/0105729 A1 | 4/2009 | Zentgraf |
| 2009/0105751 A1 | 4/2009 | Zentgraf |
| 2009/0125038 A1 | 5/2009 | Ewers et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr |
| 2009/0192598 A1 | 7/2009 | Lattouf et al. |
| 2009/0259304 A1 | 10/2009 | O'Beirne et al. |
| 2009/0326578 A1 | 12/2009 | Ewers |
| 2010/0030061 A1 | 2/2010 | Canfield et al. |
| 2010/0030242 A1 | 2/2010 | Nobles et al. |
| 2010/0042147 A1 | 2/2010 | Janovsky et al. |
| 2010/0121349 A1 | 5/2010 | Meier et al. |
| 2010/0160726 A1 | 6/2010 | Windheuser |
| 2010/0174297 A1 | 7/2010 | Speziali |
| 2010/0185172 A1 | 7/2010 | Fabro |
| 2010/0217283 A1 | 8/2010 | St. Goar |
| 2010/0298929 A1 | 11/2010 | Thornton et al. |
| 2011/0011917 A1 | 1/2011 | Loulmet |
| 2011/0202127 A1 | 8/2011 | Mauch |
| 2012/0071922 A1 | 3/2012 | Shanley |
| 2012/0184971 A1 | 7/2012 | Zentgraf et al. |
| 2013/0018393 A1* | 1/2013 | Bengtson ............ A61B 17/0682 606/139 |
| 2013/0035757 A1 | 2/2013 | Zentgraf et al. |
| 2013/0119108 A1 | 5/2013 | Altman |
| 2013/0150710 A1 | 6/2013 | Zentgraf et al. |
| 2013/0158600 A1 | 6/2013 | Conklin et al. |
| 2014/0031926 A1* | 1/2014 | Kudlik .................. A61F 2/2454 623/2.37 |
| 2014/0039324 A1 | 2/2014 | Speziali |
| 2014/0114404 A1* | 4/2014 | Gammie ............. A61B 17/0469 623/2.11 |
| 2014/0214152 A1* | 7/2014 | Bielefeld ........... A61B 17/0487 623/2.11 |
| 2014/0275757 A1* | 9/2014 | Goodwin ............ A61F 2/2466 600/37 |
| 2014/0276764 A1 | 9/2014 | Shuman |

(56) References Cited

U.S. PATENT DOCUMENTS

| | | | |
|---|---|---|---|
| 2014/0276979 A1* | 9/2014 | Sauer | A61B 17/0487 606/232 |
| 2014/0364875 A1 | 12/2014 | Zentgraf | |
| 2015/0066138 A1* | 3/2015 | Alexander | A61B 18/1492 623/2.11 |
| 2015/0148821 A1 | 5/2015 | Speziali | |
| 2015/0165189 A1* | 6/2015 | Ollivier | A61N 1/37518 607/127 |
| 2015/0190207 A1 | 7/2015 | Zentgraf et al. | |
| 2015/0216662 A1* | 8/2015 | Medema | A61B 17/0625 623/2.4 |
| 2015/0313620 A1 | 11/2015 | Suri | |
| 2015/0313713 A1 | 11/2015 | Zentgraf et al. | |
| 2015/0351741 A1 | 12/2015 | Hawkins | |
| 2015/0351910 A1 | 12/2015 | Gilmore et al. | |
| 2015/0366556 A1 | 12/2015 | Khairkhahan et al. | |
| 2016/0106420 A1 | 4/2016 | Foerster et al. | |
| 2016/0143737 A1 | 5/2016 | Zentgraf et al. | |
| 2016/0151183 A1* | 6/2016 | Nishigishi | A61F 2/966 623/1.12 |
| 2017/0157391 A1 | 6/2017 | Ollivier | |
| 2017/0245994 A1 | 8/2017 | Khairkhahan et al. | |
| 2017/0290582 A1 | 10/2017 | Speziali | |
| 2018/0125657 A1* | 5/2018 | Dahlgren | A61F 2/2466 |
| 2018/0161035 A1 | 6/2018 | Greenberg et al. | |
| 2018/0243087 A1* | 8/2018 | Kapadia | A61F 2/246 |
| 2018/0280138 A1 | 10/2018 | Colli | |
| 2018/0289483 A1 | 10/2018 | Kang et al. | |
| 2018/0318083 A1* | 11/2018 | Bolling | A61M 25/0054 |
| 2019/0053902 A1 | 2/2019 | Zentgraf et al. | |
| 2019/0133766 A1 | 5/2019 | Zentgraf et al. | |
| 2019/0224012 A1 | 7/2019 | Colli | |
| 2019/0290260 A1 | 9/2019 | Caffes et al. | |
| 2019/0290434 A1* | 9/2019 | Stearns | A61F 2/2469 |
| 2019/0343626 A1 | 11/2019 | Smirnov et al. | |
| 2019/0343633 A1 | 11/2019 | Garvin et al. | |
| 2019/0343634 A1 | 11/2019 | Garvin et al. | |
| 2019/0381325 A1 | 12/2019 | Regnier | |
| 2019/0388218 A1* | 12/2019 | Vidlund | A61F 2/2409 |
| 2020/0093478 A1 | 3/2020 | Caffes et al. | |
| 2020/0093644 A1* | 3/2020 | Kraitzer | A61F 11/006 |
| 2020/0107933 A1* | 4/2020 | Oba | A61F 2/246 |
| 2020/0121314 A1 | 4/2020 | Speziali | |
| 2020/0138430 A1 | 5/2020 | Zentgraf | |
| 2020/0188108 A1* | 6/2020 | Grimm | A61F 2/2445 |
| 2020/0222186 A1 | 7/2020 | Edmiston et al. | |
| 2020/0281582 A1 | 9/2020 | Caffes et al. | |
| 2020/0297489 A1 | 9/2020 | Bishop | |
| 2020/0330228 A1* | 10/2020 | Anderson | A61F 2/2457 |
| 2020/0383784 A1 | 12/2020 | Albes | |
| 2021/0220130 A1* | 7/2021 | Rajagopal | A61F 2/2466 |
| 2021/0220138 A1* | 7/2021 | Edmiston | A61F 2/2457 |
| 2022/0039833 A1* | 2/2022 | Thai | A61M 25/04 |
| 2022/0226117 A1* | 7/2022 | Colli | A61F 2/2457 |
| 2022/0338990 A1* | 10/2022 | Hamill | A61F 2/2454 |
| 2023/0101706 A1* | 3/2023 | Morrison | A61B 17/0642 623/13.14 |

FOREIGN PATENT DOCUMENTS

| | | |
|---|---|---|
| EP | 1845861 A2 | 10/2007 |
| EP | 1408850 B1 | 9/2009 |
| EP | 3441045 A1 | 2/2019 |
| JP | H 04307052 A | 10/1992 |
| JP | 06142114 | 5/1994 |
| JP | 2004-531337 | 10/2004 |
| JP | 2007-535342 | 12/2007 |
| WO | WO 1999/00059 A1 | 1/1999 |
| WO | WO 1999/30647 A1 | 6/1999 |
| WO | WO 2000/06026 A2 | 2/2000 |
| WO | WO 2000/06027 A2 | 2/2000 |
| WO | WO 2000/06028 A1 | 2/2000 |
| WO | WO 2000/16700 A1 | 3/2000 |
| WO | WO 2001/66018 A1 | 9/2001 |
| WO | WO 2001/95809 A1 | 12/2001 |
| WO | WO 2003/001893 A2 | 1/2003 |
| WO | WO 2003/059209 A2 | 7/2003 |
| WO | WO 2003/079937 A2 | 10/2003 |
| WO | WO 2003/082157 A2 | 10/2003 |
| WO | WO 2003/082158 A1 | 10/2003 |
| WO | WO 2004/021893 A1 | 3/2004 |
| WO | WO 2004/043265 A2 | 5/2004 |
| WO | WO 2005/039428 A2 | 5/2005 |
| WO | WO 2005/087140 A1 | 9/2005 |
| WO | WO 2005/094525 A2 | 10/2005 |
| WO | WO 2006/012750 A1 | 2/2006 |
| WO | WO 2006/032051 A2 | 3/2006 |
| WO | WO 2006/065966 A2 | 6/2006 |
| WO | WO 2006/078694 A2 | 7/2006 |
| WO | WO 2006/116310 A2 | 11/2006 |
| WO | WO 2006/127509 A2 | 11/2006 |
| WO | WO 2007/002627 A1 | 1/2007 |
| WO | WO 2007/027451 A2 | 3/2007 |
| WO | WO 2007/062128 A2 | 5/2007 |
| WO | WO 2007/081418 A1 | 7/2007 |
| WO | WO 2007/117612 A1 | 10/2007 |
| WO | WO 2008/010738 A2 | 1/2008 |
| WO | WO 2009/052528 A2 | 4/2009 |
| WO | WO 2011/070477 A1 | 6/2011 |
| WO | WO 2011/137336 A1 | 11/2011 |
| WO | WO 2012/167120 A2 | 12/2012 |
| WO | WO 2018/236766 A1 | 12/2018 |
| WO | WO 2019/217638 A1 | 1/2020 |

OTHER PUBLICATIONS

Machine translation of JP 06142114.
Port Access System for Mitral Valve Repair Proves Its Value in Study; MedGadget Jul. 9, 2009 (2 pages).
PCT/US2020/028532, Search Report and Written Opinion, dated Jul. 1, 2020, 7 pages.
Application and File History for U.S. Appl. No. 11/813,695, filed Jul. 11, 2007, now U.S. Pat. No. 8,465,500. Inventor: Speziali.
Application and File History for U.S. Appl. No. 12/709,220, filed Feb. 19, 2010, now U.S. Pat. No. 8,968,338. Inventor: Speziali.
Application and File History for U.S. Appl. No. 13/898,709, filed May 21, 2013, now U.S. Pat. No. 9,364,213. Inventors: Speziali.
Application and File History for U.S. Appl. No. 13/339,865, filed Dec. 29, 2011, now U.S. Pat. No. 9,044,221. Inventors: Zentgraf et al.
Application and File History for U.S. Appl. No. 13/340,185, filed Dec. 29, 2011. Inventors: Zentgraf et al.
Application and File History for U.S. Appl. No. 14/707,945, filed May 8, 2015. Inventors: Zentgraf et al.
Application and File History for U.S. Appl. No. 12/254,808, filed Oct. 20, 2008, now U.S. Pat. No. 9,192,374. Inventor: Zentgraf.
Application and File History for U.S. Appl. No. 12/254,807, filed Oct. 20, 2008, now U.S. Pat. No. 8,758,393. Inventor: Zentgraf.
Application and File History for U.S. Appl. No. 14/310,069, filed Jun. 20, 2014. Inventor: Zentgraf.
Application and File History for U.S. Appl. No. 16/137,734, filed Sep. 21, 2018. Inventor: Zentgraf et al.
Application and File History for U.S. Appl. No. 16/191,565, filed Nov. 15, 2018. Inventor: Zentgraf et al.
Application and File History for U.S. Appl. No. 13/486,632, filed Jun. 1, 2012. Inventor Zentgraf et al.
Application and File History for U.S. Appl. No. 13/692,027, filed Dec. 3, 2012. Inventors: Zentgraf et al.
Application and File History for U.S. Appl. No. 14/947,399, filed Nov. 20, 2015. Inventors: Zentgraf et al.
Application and File History for U.S. Appl. No. 16/905,645, filed Jun. 18, 2020. Inventors: Zentgraf et al.
Application and File History for U.S. Appl. No. 14/614,570, filed Feb. 5, 2015. Inventors: Speziali.
Application and File History for U.S. Appl. No. 16/406,736, filed May 8, 2019. Inventors: Smirnov et al.
Application and File History for U.S. Appl. No. 16/406,764, filed May 8, 2019. Inventors: Garvin et al.

(56) References Cited

OTHER PUBLICATIONS

Application and File History for U.S. Appl. No. 16/406,799, filed May 8, 2019. Inventors: Garvin et al.
Application and File History for U.S. Appl. No. 16/818,639, filed Mar. 13, 2020. Inventors: Caffes et al.
Application and File History for U.S. Appl. No. 16/363,701, filed Mar. 25, 2019. Inventors: Caffes et al.

* cited by examiner

TRANSVERSE HELICAL CARDIAC ANCHOR FOR MINIMALLY INVASIVE HEART VALVE REPAIR

RELATED APPLICATION

This application is a continuation of U.S. application Ser. No. 16/850,827 filed Apr. 16, 2020, which claims the benefit of U.S. Provisional Application No. 62/834,512 filed Apr. 16, 2019, which is hereby fully incorporated herein by reference.

TECHNICAL FIELD

The present invention relates to minimally invasive delivery of a suture into the heart. More particularly, the disclosed embodiments relate to inserting and anchoring one or more sutures as artificial chordae tendineae for a flailing or prolapsing leaflet in a beating heart.

BACKGROUND

The mitral and tricuspid valves inside the human heart include an orifice (annulus), two (for the mitral) or three (for the tricuspid) leaflets and a subvalvular apparatus. The subvalvular apparatus includes multiple chordae tendineae, which connect the mobile valve leaflets to muscular structures (papillary muscles) inside the ventricles. Rupture or elongation of the chordae tendineae results in partial or generalized leaflet prolapse, which causes mitral (or tricuspid) valve regurgitation. A commonly used technique to surgically correct mitral valve regurgitation is the implantation of artificial chordae (usually 4-0 or 5-0 Gore-Tex sutures) between the prolapsing segment of the valve and the papillary muscle.

This technique for implantation of artificial chordae was traditionally done by an open heart operation generally carried out through a median sternotomy and requiring cardiopulmonary bypass with aortic cross-clamp and cardioplegic arrest of the heart. Using such open heart techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of an artificial chordae through the atriotomy for attachment within the heart. However, these invasive open heart procedures in which the heart is stopped beating produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of such open heart techniques.

Techniques for minimally invasive thoracoscopic repair of heart valves while the heart is still beating have also been developed. U.S. Pat. No. 8,465,500 to Speziali, which is incorporated by reference herein, discloses a thoracoscopic heart valve repair method and apparatus. Instead of requiring open heart surgery on a stopped heart, the thoracoscopic heart valve repair methods and apparatus taught by Speziali utilize fiber optic technology in conjunction with transesophageal echocardiography (TEE) as a visualization technique during a minimally invasive surgical procedure that can be utilized on a beating heart. More recent versions of these techniques are disclosed in U.S. Pat. Nos. 8,758,393 and 9,192,374 to Zentgraf, which are also incorporated by reference herein and disclose an integrated device that can enter the heart chamber, navigate to the leaflet, capture the leaflet, confirm proper capture, and deliver a suture as part of a mitral valve regurgitation (MR) repair. In some procedures, these minimally invasive repairs are generally performed through a small, between the ribs access point followed by a puncture into the ventricle through the apex of the heart. Although far less invasive and risky for the patient than an open heart procedure, these procedures still require significant recovery time and pain.

Some systems have therefore been proposed that utilize a catheter routed through the patient's vasculature to enter the heart and attach a suture to a heart valve leaflet as an artificial chordae. While generally less invasive than the approaches discussed above, transcatheter heart valve repair can provide additional challenges. For example, with all artificial chordae replacement procedures, in addition to inserting a suture through a leaflet, the suture must also be anchored at a second location, such as at a papillary muscle in the heart, with a suture length, tension and positioning of the suture that enables the valve to function naturally. If the suture is too short and/or has too much tension, the valve leaflets may not properly close. Conversely, if the suture is too long and/or does not have enough tension, the valve leaflets may still be subject to prolapse. Proper and secure anchoring of the suture away from the leaflet is a critical aspect of any heart valve repair procedure for inserting an artificial chordae.

In the case of transcatheter procedures for heart valve repair procedures, some cardiac anchors that are used are similar to the kind of longitudinal helical or cork screw type anchors used for securing pacing and defibrillation leads as shown, for example, in U.S. Pat. No. 9,877,833. Unfortunately, properly and securely anchoring of the suture for transcatheter heart valve repair procedures is further complicated because it can be difficult for the flexible catheter required for routing through the patient's vasculature to apply sufficient force to stably insert traditional anchors perpendicularly into the heart wall, e.g., the myocardium. This complication can be particularly true in the case of mitral valve repairs that require access to the left ventricle for insertion of the anchor in that following a typical intravascular access to the right atrium, the flexible catheter must additionally be routed across the septum into the left atrium and then down across the valve into the left ventricle.

SUMMARY

Disclosed herein are various embodiments of cardiac anchors configured to be inserted into a heart wall of a patient to anchor a suture as an artificial chordae under an appropriate tension for proper valve function. Such cardiac anchors are particularly suitable for use in intravascular, transcatheter procedures. In particular, the anchors disclosed herein are beneficial in mitral valve repairs to have sufficient force and proper alignment for anchoring in the left ventricle. In some embodiments, the cardiac anchor delivery and implantation tools and techniques provide sufficient force and alignment after transseptal access to the left atrium and crossing of the mitral valve into the left ventricle in order to effectively secure the anchor without damage to the myocardial wall in the left ventricle.

In one embodiment, a cardiac anchor is configured to be implanted transversely into and along a patient's heart wall to anchor a suture extending from a valve leaflet of the heart as an artificial chordae. The anchor can include an anchor body including an actuation head at a proximal end of the anchor body configured to be engaged by an actuation tool to enact rotation of the anchor body. The anchor can further include a coil extending around at least a portion of the anchor body and distally of the anchor body. The coil can have a distal tip configured to be driven into the heart wall. A stabilizing element can extend from the anchor body distally through the coil such that the stabilizing extends distally beyond the coil to align the coil at a predetermined orientation relative to the heart wall. In an embodiment, the stabilizing element can include a flexible shaft and a blunt tip can be positioned at a distal end of the flexible shaft.

In one embodiment, a method of anchoring a suture in a patient's heart as an artificial chordae includes intravascularly accessing a patient's heart and inserting a suture into a heart valve leaflet of the patient's heart. A portion of the suture can be attached to a cardiac anchor that can include an actuation head at a proximal end of an anchor body, a coil extending distally of the anchor body having a distal tip, and a stabilizing element extending from the anchor body distally through the coil. The anchor can be advanced to a heart wall of the heart with an anchor delivery catheter and an actuation mechanism engaged with the actuation head to rotate the anchor. Actuating the anchor can drive the stabilizing element against the heart wall orient the coil in a predetermined orientation relative to the heart wall such that further actuation of the anchor to rotate the coil will cause the distal tip of the coil to enter the heart wall and further rotation of the coil causes the coil to become embedded along the heart wall in a predetermined orientation relative to the heart wall.

In embodiments, the actuation mechanism of the anchor delivery catheter includes an anchor driver having a distal end that mates with corresponding geometry within a proximal portion of the anchor body. In some embodiments, the anchor driver is configured to mate with the proximal portion of the anchor body such that the anchor driver is coaxially aligned with the flexible shaft and the anchor body while rotatably driving the anchor body which in turn causes the anchor coil to be rotated. In some embodiments, the anchor driver is configured to be mated with the anchor body such that the anchor body and the anchor driver maintain coaxial alignment during operation of the anchor driver in order to better facilitate control of the orientation of the flexible shaft relative to the myocardial wall. In some embodiments, the anchor driver rotates only the anchor body and does not rotate the flexible shaft. In some embodiments, a stiffening tube coaxial surrounds both the anchor driver and the flexible shaft to provide better alignment and control of delivery of the anchor coil.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
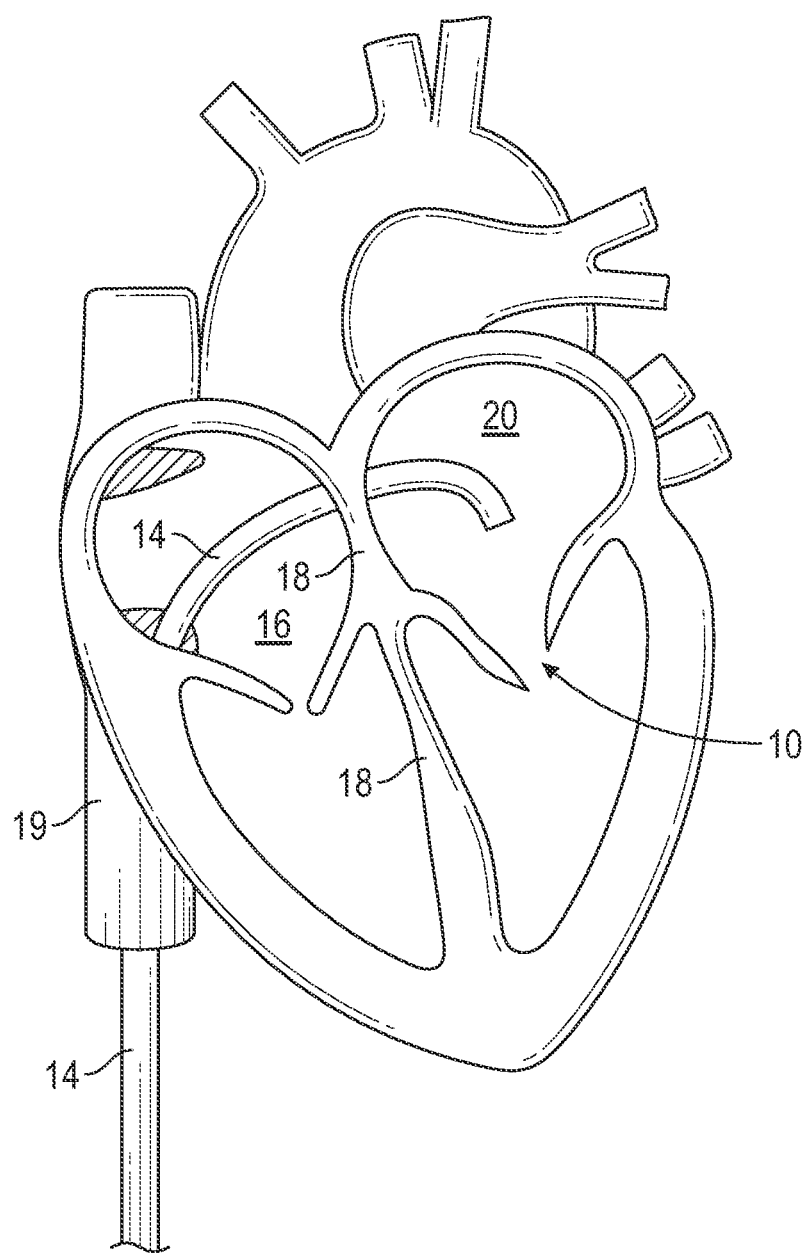
FIG. 1 is a schematic representation of a method for inserting a leaflet capture catheter into a beating heart of a patient according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The present disclosure is generally directed to inserting and anchoring one or more sutures as artificial chordae into one or more heart valve leaflets through an intravascular, transcatheter approach. A heart valve leaflet may be captured and a suture inserted through the leaflet in any manner known in the art. Examples of such leaflet capture catheters are disclosed in copending U.S. Patent Publication Nos. 2019/0290260 and 2020/0093478, each of which is hereby incorporated by reference herein. Other transcatheter procedures for inserting an artificial chordae are disclosed in U.S. Patent Publication No. 2016/0143737 and U.S. patent application Ser. No. 16/745,074, each of which is hereby incorporated by reference herein.

Access into the heart to the valve being repaired can be gained through an intravascular, transcatheter approach. If the valve being repaired is the mitral valve, the valve may further be accessed transseptally. FIG. 1 depicts a schematic representation of an embodiment of an access approach for a heart valve repair system accessing the mitral valve 10. FIG. 1 depicts a guide catheter 14 accessing the interior of the heart via the femoral vein. In some embodiments, such a system can further include an outer guide catheter and an inner guide catheter. In such embodiments, the outer guide catheter can be inserted into the femoral vein at the patient's groin and advanced through the femoral vein into the inferior vena cava 19 and then into the right atrium 16. In various embodiments, the outer guide catheter can be steerable in a single plane and can have an outer diameter of about or less than about 30 french, such as, for example 24 french. The septum 18 can then be punctured using an appropriate puncture tool and the outer guide catheter advanced into the septum 18 or through the septum 18 into the left atrium 20. The inner guide catheter can then be axially advanced through the outer guide catheter into the left atrium 20. In some embodiments, the inner guide catheter can have two plans of steerability and can be maneuvered along with and/or beyond the outer guide catheter to establish a stable position superior to the mitral valve 10 and to provide a desired trajectory for operation of a leaflet capture catheter to repair the valve. In other embodiments, anchors as described herein may be implanted through other intravascular approaches as well as non-intravascular approaches.

Referring to FIGS. 2A-2K, a procedure for anchoring a suture inserted as an artificial chordae in a transcatheter procedure on a beating heart of a patient following insertion of the suture into a leaflet is schematically depicted. In this embodiment, a loop of suture has been inserted through the leaflet and the two free ends of the suture then inserted through the loop to form a girth hitch knot around the edge of the leaflet. Further detail regarding attaching a suture to a leaflet in this manner can be found in U.S. Patent Publication No. 2017/0290582, which is hereby incorporated by reference herein.

Figure 2A:
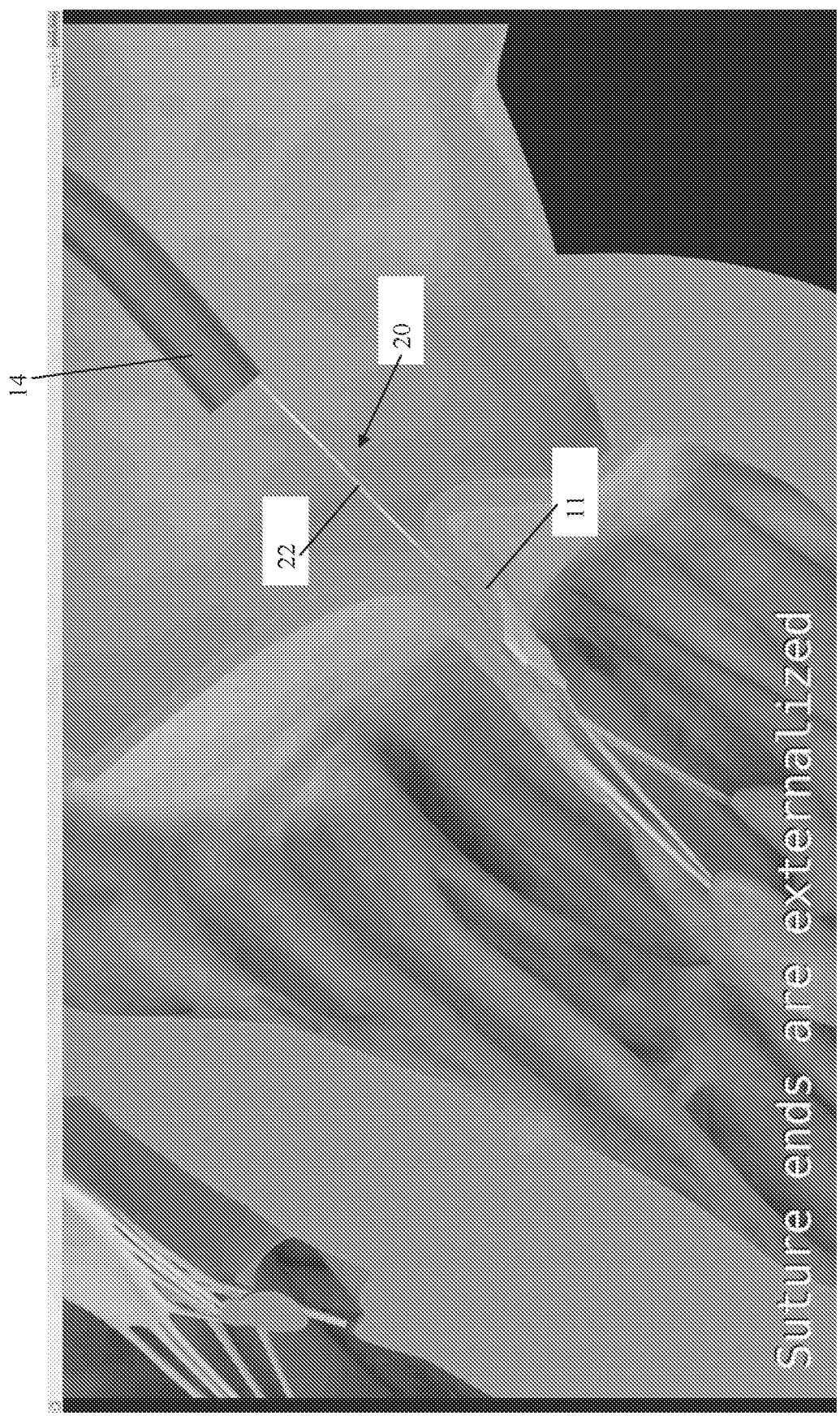
FIGS. 2A-2K depict various steps in a method of anchoring a suture in a beating heart of a patient to function as an artificial chordae according to an embodiment.
Figure 2B:
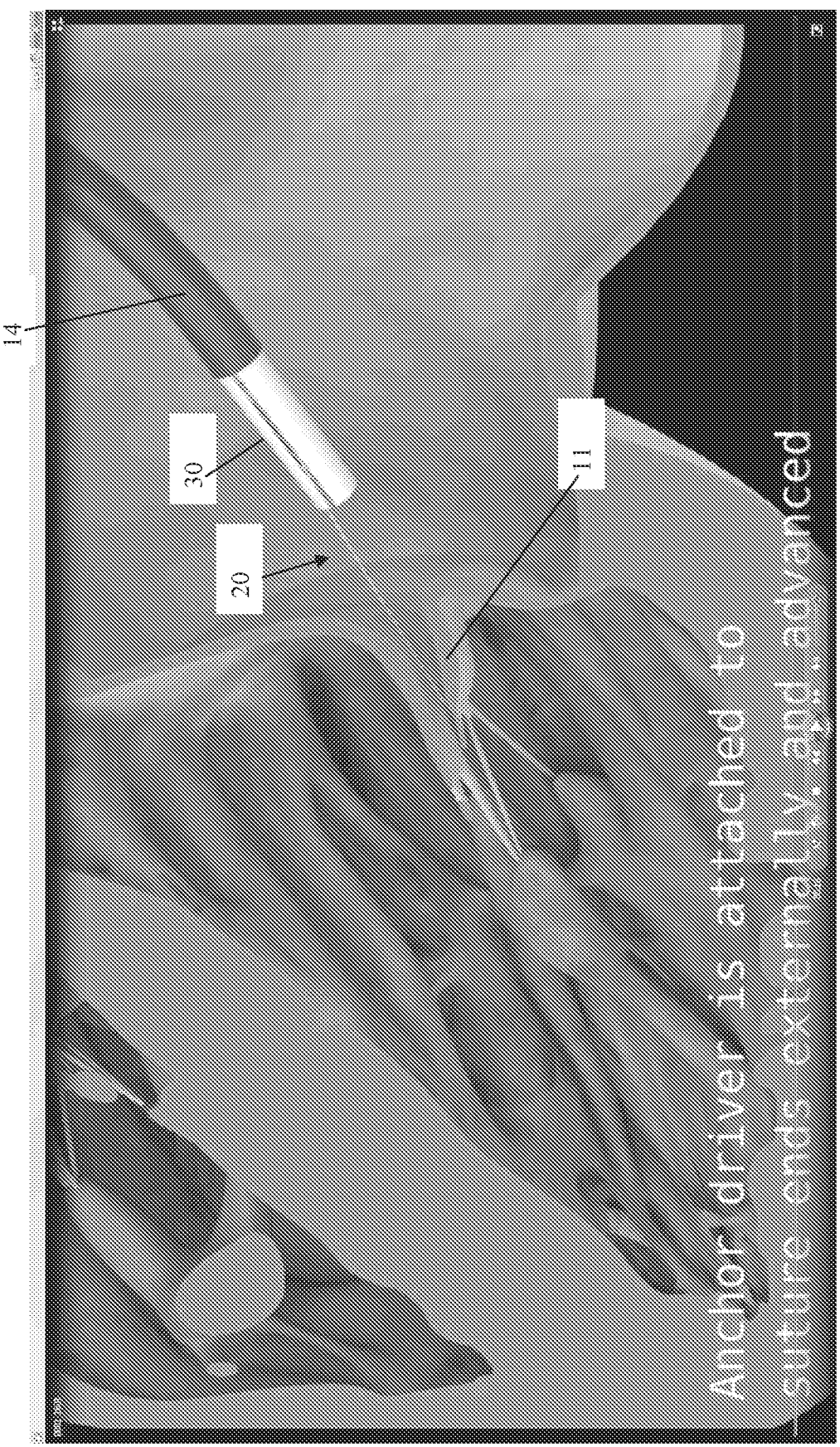
Figure 2C:
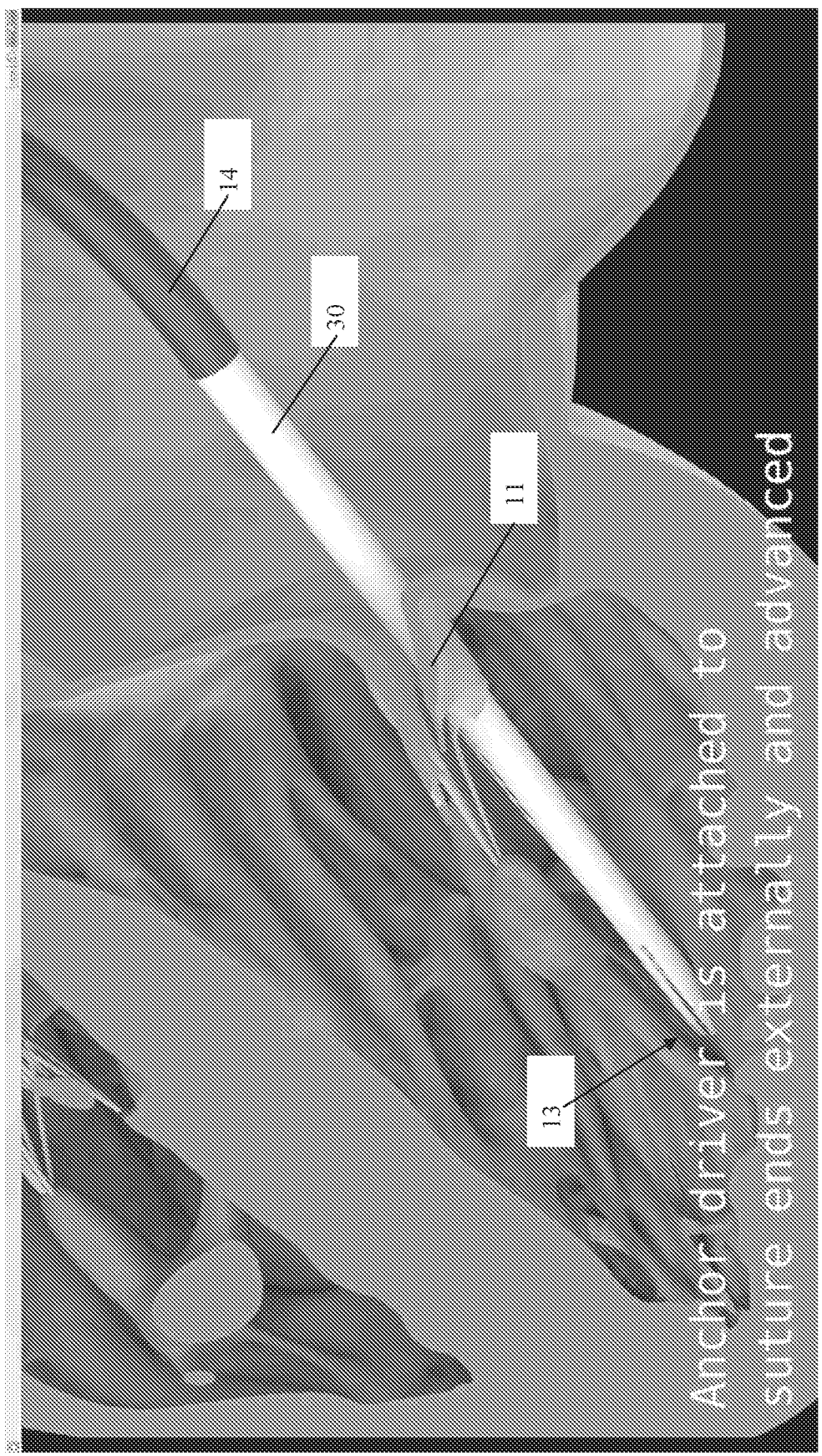
Figure 2D:
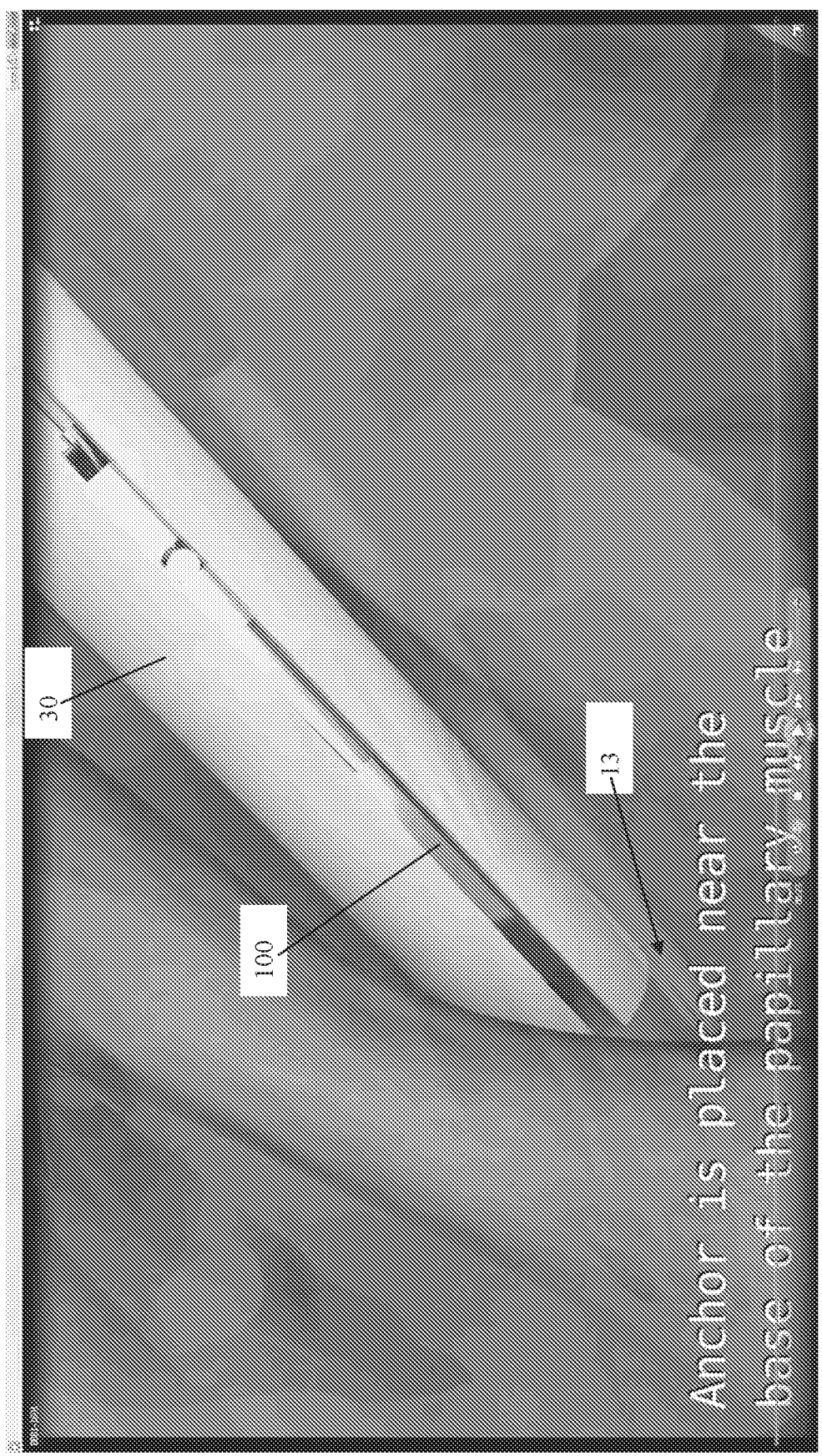
Figure 2E:
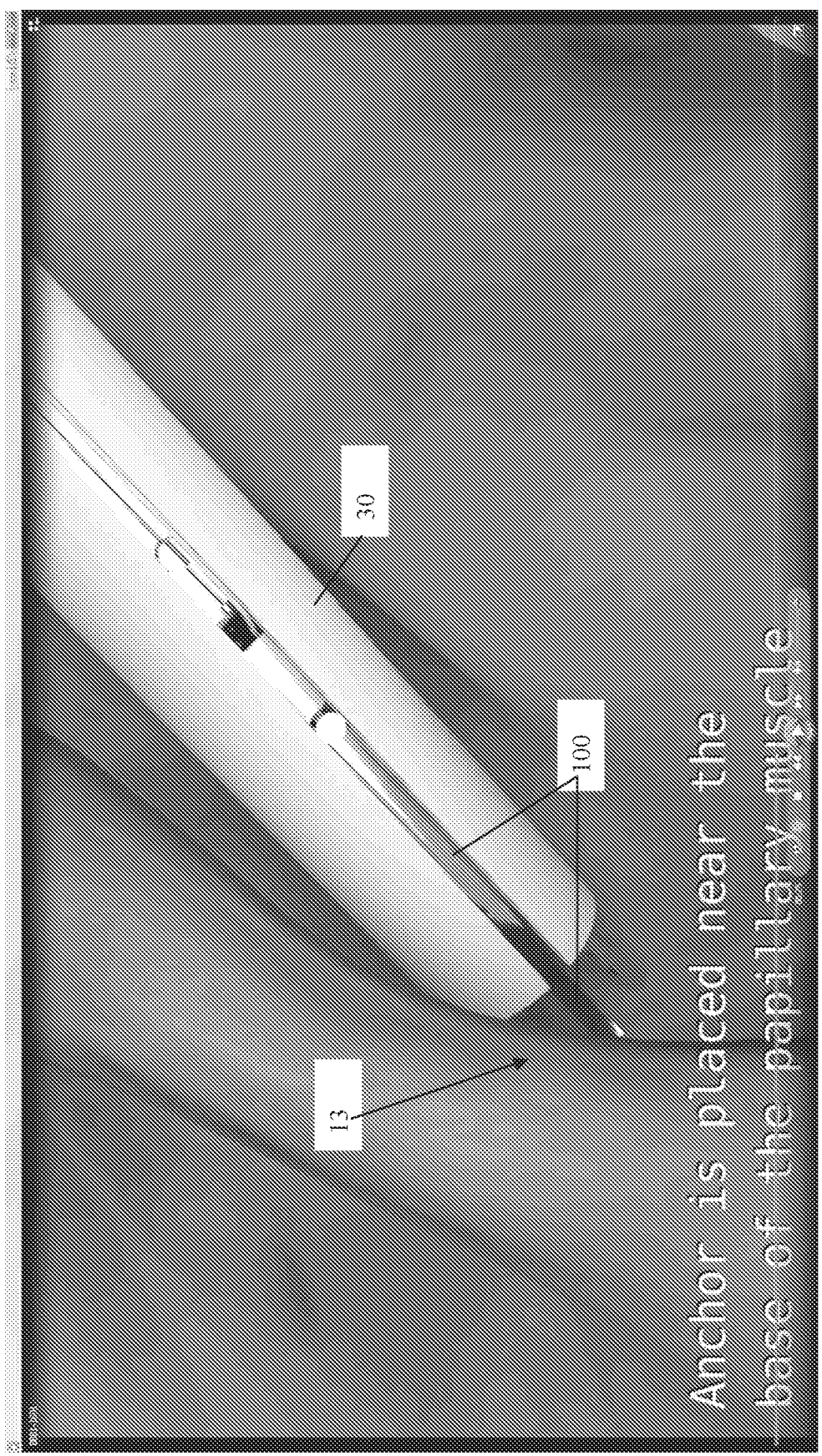
Figure 2F:
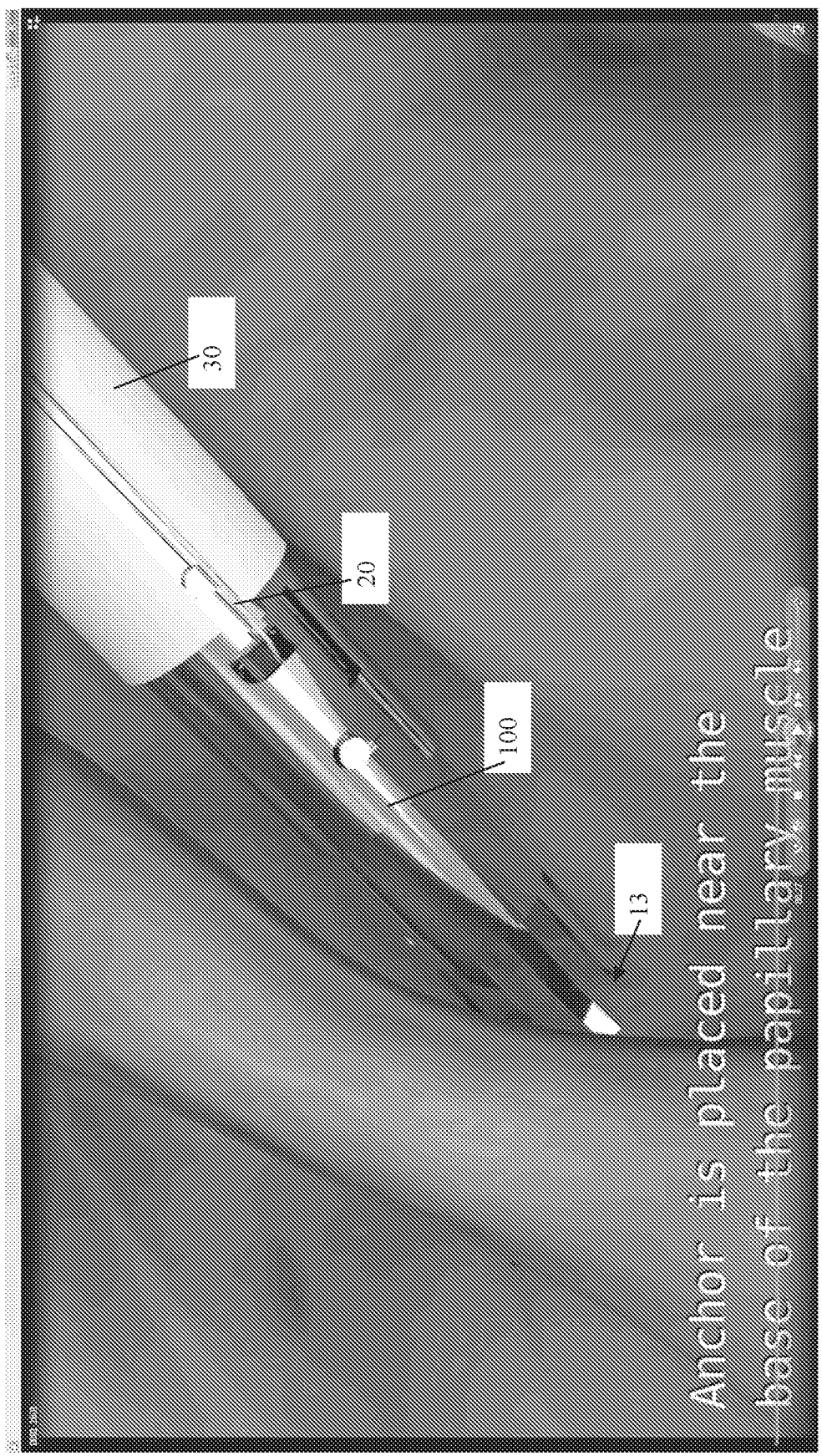
Figure 2G:

In embodiments, following insertion of the suture 20 into the leaflet 11, the deployment catheter used to insert the suture is withdrawn through the guide catheter 14 and the two free ends 22 of the suture 20 are also withdrawn external to the body. The suture ends 22 are then attached to a cardiac anchor contained in an anchor driving catheter 30. Alternatively, the anchor could be pre-attached to the suture prior to insertion of the suture into the leaflet. The anchor driving catheter 30 is inserted into the guide catheter 14, routed through the catheter into the body and advanced past the leaflet 11 to the heart wall 13 below the valve at, for example, a papillary muscle as shown in FIGS. 2B-2D. The anchor driving catheter 30 is then used to insert a cardiac anchor 100 into the myocardium as shown in FIGS. 2D-2G and as described in more detail below.

Figure 2H:
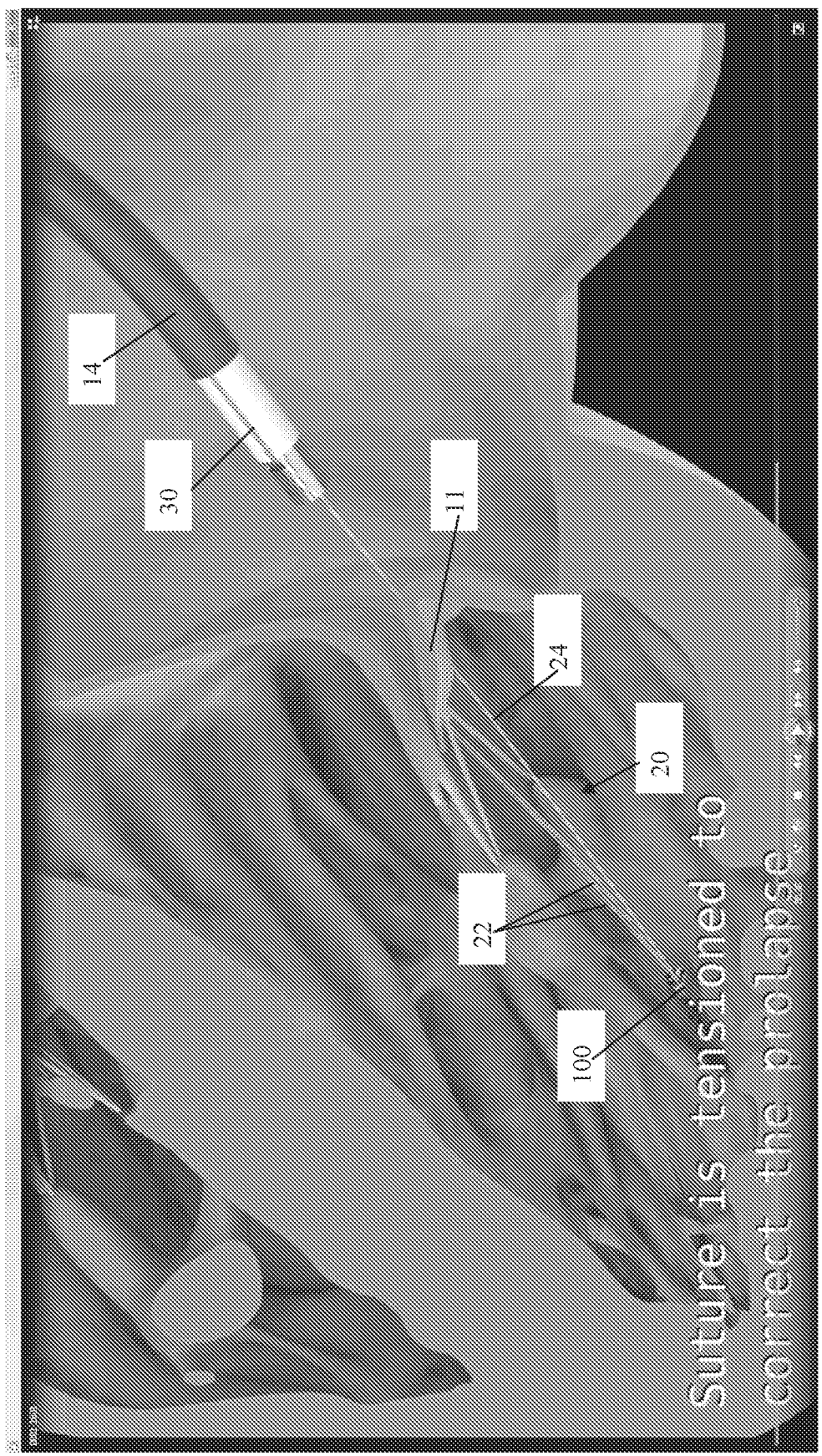
Figure 2I:
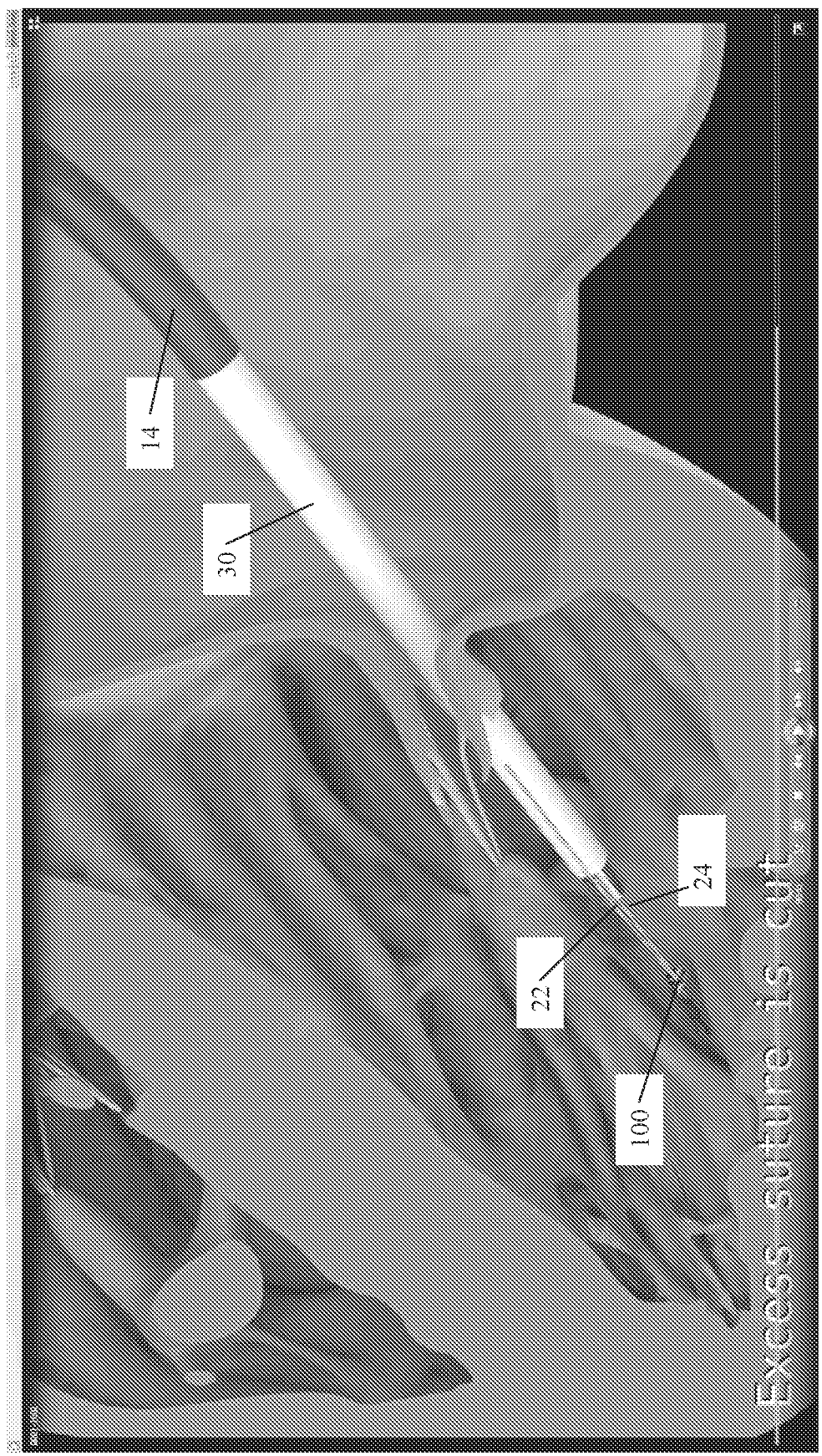
Figure 2J:
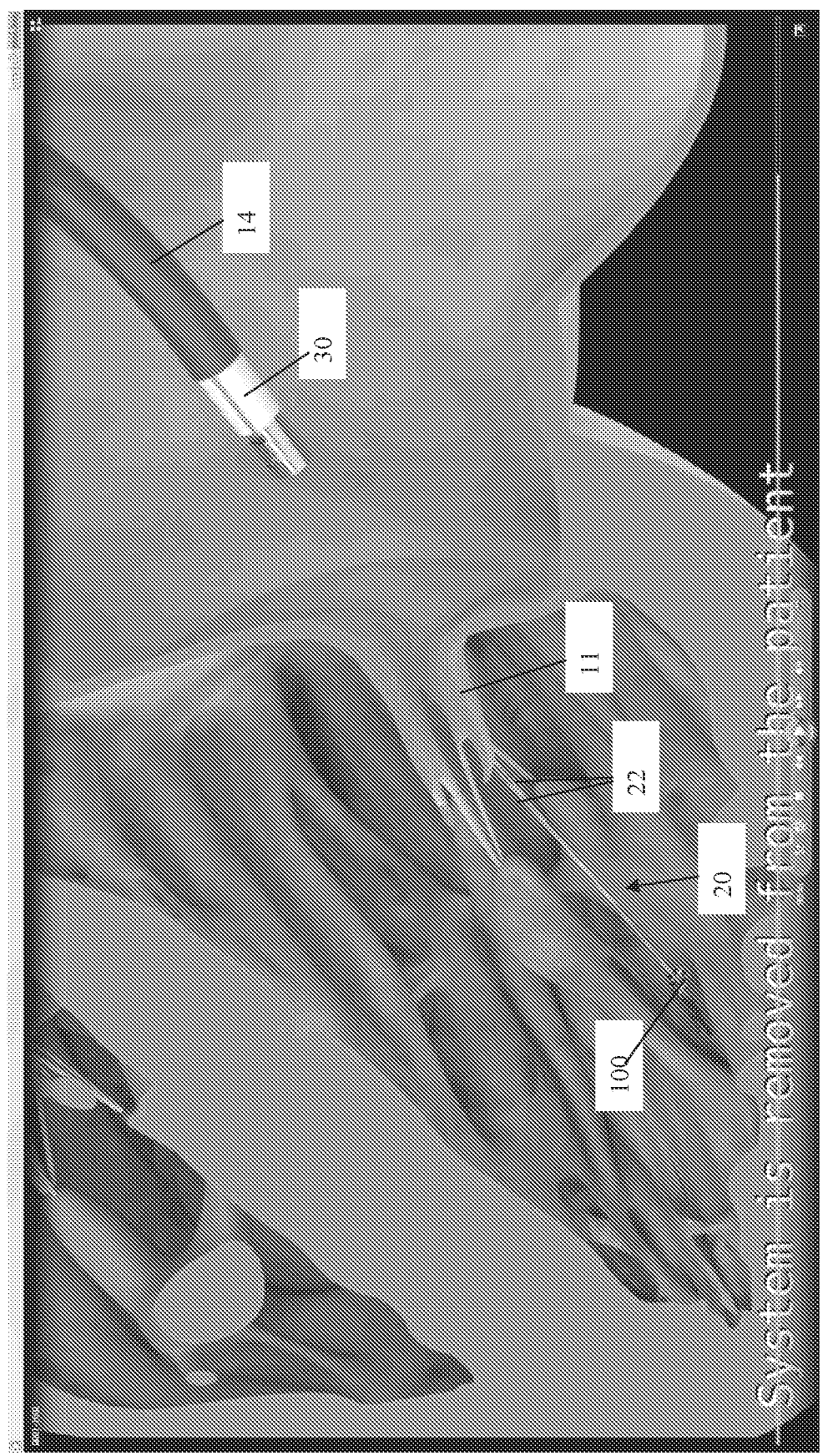
Figure 2K:

In various embodiments, after insertion of the cardiac anchor 100 into the heart tissue, the anchor driving catheter 30 is withdrawn to a position superior of the valve as shown in FIG. 2H and the length and tension of the suture ends 22 extending from the leaflet 11 are tested and adjusted until it is determined that normal valve function has been achieved. This determination can be made through use of ultrasonic imaging, for example. The tension is adjusted through a tensioning strand 24 of the suture depicted in FIG. 2H. Once the proper length and tension has been determined using, for example, transesophageal echocardiography or other non-invasive methods, the anchor driving catheter 30 is advanced back down along the tensioning strand 24 and to sever the strand at the anchor 100. The entire catheter system, including the anchor driving catheter 30 and the guide catheter 14 is then withdrawn from the patient's body. Referring to FIG. 2K, the suture 20 remains in the body extending between the leaflet 11 and the anchor 100 to function as an artificial chordae tendineae Disclosed herein are various embodiments of cardiac anchors that can be employed in procedures such those described above to anchor a suture as an artificial chordae. Such anchors maintain positioning and length of the suture (i.e., tension) to ensure proper leaflet functionality during the cardiac cycle.

Figure 3A:
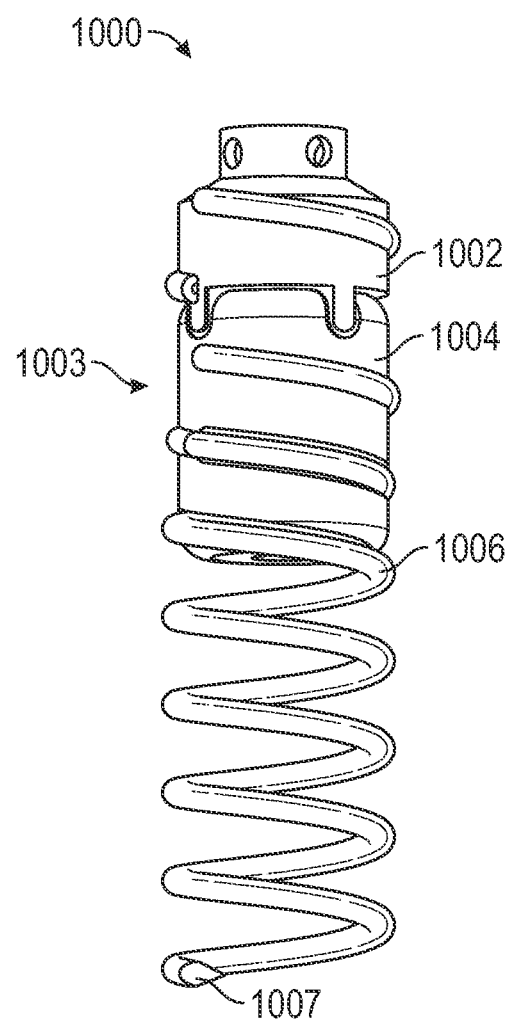
FIGS. 3A-3C depict an anchor system for an artificial chordae according to an embodiment.
Figure 3B:
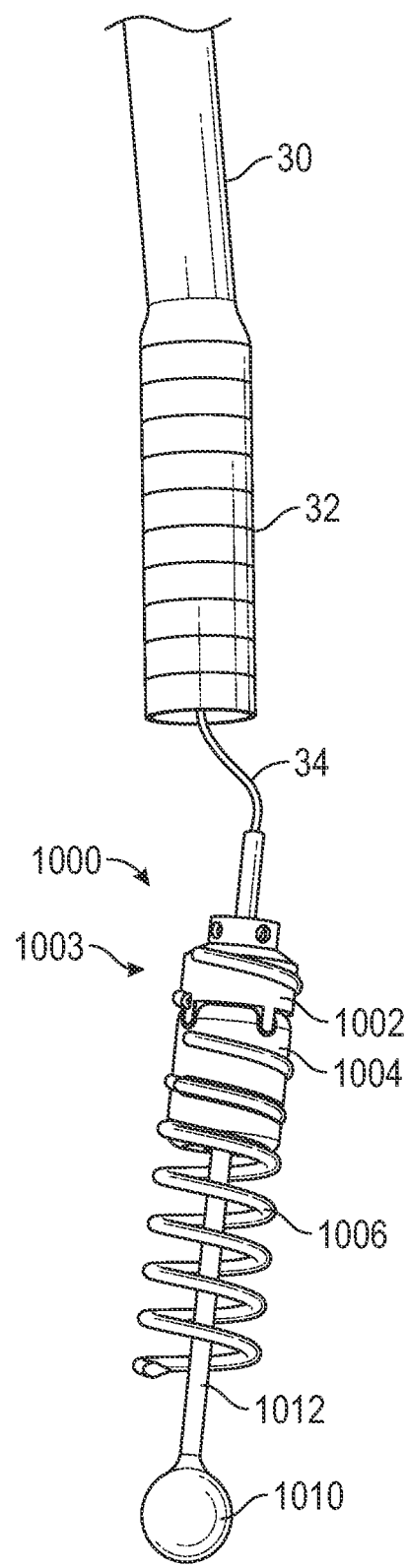
Figure 3C:
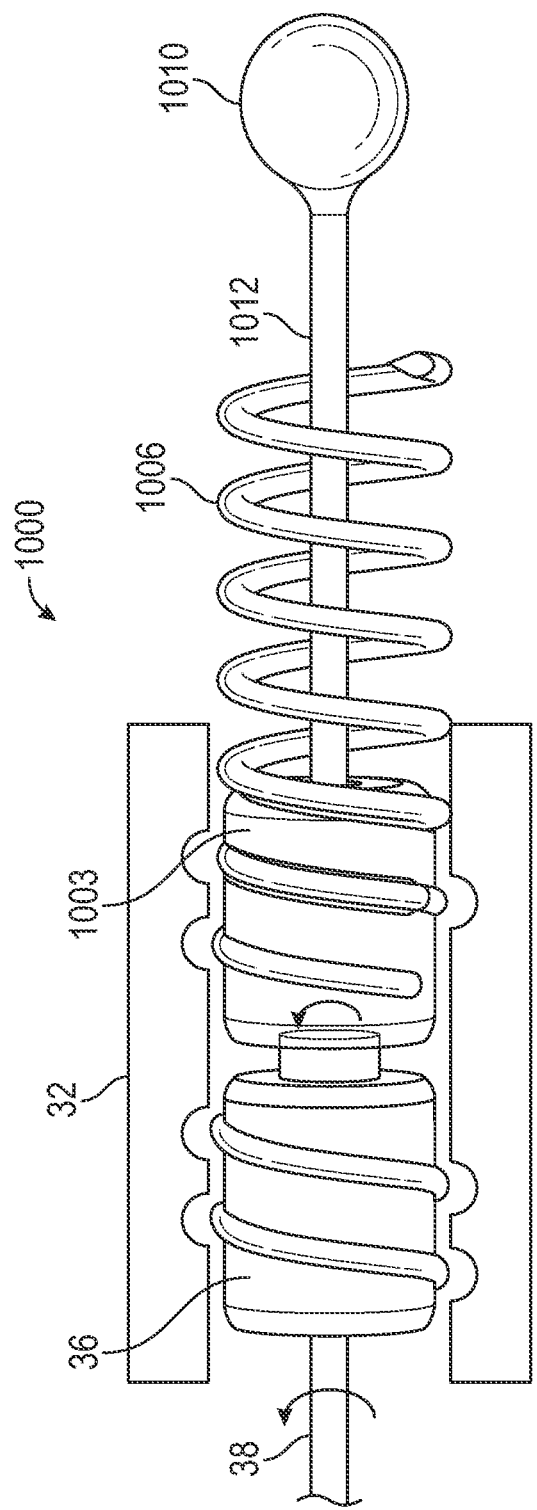

Referring now to FIGS. 3A-3C, one embodiment of a cardiac anchor 1000 that can be seated transversely along the heart wall to anchor a suture extending from a valve leaflet to function as an artificial chordae according to an embodiment is depicted. Anchor 1000 generally includes an anchor body 1003 having a screw head 1002 and an anchor dock 1004 and an anchor coil 1006. The screw head 1002 can be attached to the anchor dock 1004 and the coil 1006 can connect to and extend around an outer perimeter of the anchor body 1003 to provide a generally threaded configuration on the exterior of the anchor body 1003. Coil 1006 can include a sharp distal tip 1007 configured to be transversely driven into and along the heart tissue. Referring to FIG. 3B, anchor 1000 can also generally include an atraumatic or blunt tip 1010 connected to a flexible shaft 1012 that can extend from or through the anchor dock 1004 and/or screw head 1002. The flexible shaft 1012 can extend through the anchor coil 1006 such that the atraumatic tip 1010 extends distally of the coil 1006. In some embodiments, the flexible shaft 1012 is longitudinally fixed with respect to the screw head 1002, such that there is a set and constant distance between the atraumatic tip 1010 and the distal end of the coil 1006. In other embodiments, the flexible shaft 1012 can be configured to be slidable within the screw head 1002 to enable the distance between the atraumatic tip 1010 and the distal end of the coil 1006 to be adjusted as necessary. In such embodiments, connections through the delivery catheter 30 can be maintained to enable this functionality prior to release of the anchor from the sleeve 32.

Still referring to FIG. 3B, anchor 1000 can be anchored in the heart with an anchor delivery catheter 30. In embodiments, anchor delivery catheter 30 can cooperate with a sleeve 32 specially designed to interface with anchor 1000 and a flexible guide rail 34 for guiding the anchor 1000 through the catheter 30. FIG. 3C depicts further details of sleeve 32. Sleeve 32 can comprise a thin walled tube having internal threading that mates with the threads on both the anchor dock and/or screw head 1002, 1004 as well as threads on a screw driver 36 that interfaces with the screw head 1002. Sleeve 32 functions to maintain the screw driver 36 and anchor body 1003 positioning relative to each other while allowing a smooth and controlled deployment of the anchor coil 1006. The guide rail 34 can be a suture or other suitable guidewire material that functions to enable a suture lock to be passed through the system and to the anchor body 1003, as will be described below. The guide rail 34 can also provide a reactionary force during the locking of the sutures. In other embodiments, the anchor 100 can be delivered without the guide rail 34. The screw driver 36 can be connected to a torqueable cable 38. In one embodiment, cable 38 is a Nitinol wire. The screw driver 36 is rotated by twisting the torqueable cable 38. When the screw driver 36 is rotated while in contact with the screw head 1002, it causes smooth and controlled deployment of the anchor 1000 from the sleeve 32 into the heart tissue.

The anchor coil 1006 is configured to be deployed transversely into and along the tissue of the heart wall by rotation of the screw driver 36 to provide the anchoring point for the suture attached to the leaflet to function as an artificial chordae. As will be described in greater detail herein, the anchor coil 1006 is designed to be deployed at a transverse or generally parallel angle to the heart tissue rather than driving the anchor generally perpendicularly into the heart wall tissue. This configuration provides the advantage of requiring a greater pull out force for the anchor to become dislodged from the tissue and also reduces the risk of the anchor perforating through the ventricular wall. Generally parallel or transverse deployment also embeds more of the anchor into the tougher inner layer of the myocardium known as the endocardium. The atraumatic tip 1010 and flexible shaft 1012 set the trajectory of the anchor coil 1006 to ensure generally parallel or transverse insertion into the tissue.

In embodiments, the atraumatic tip 1010 is configured as a ball or sphere and the flexible shaft 1012 is configured as a flexible coil. As discussed below, upon deployment from the sleeve 32, the tip 1010 and shaft 1012 flex against the ventricle wall to automatically set the trajectory. This limits the need for the surgeon to actively manipulate the system to establish a proper trajectory because the anchor coil 1006 will naturally follow the trajectory set up by the tip 1010 and shaft 1012. In addition, the tip 1010 can be configured to be highly visible when employing non-invasive imaging techniques such as, for example, fluoroscopy or ultrasound, to enable precise positioning of the tip 1010 and corresponding coil 1006 within the heart. The shaft 1012 in combination with the tip 1010 also establishes a set and reliable depth of the penetration of the anchor coil 1006 into the tissue.

In some embodiments, the shaft 1012 may also have a variable flexibility along its length with the shaft being more flexible at distal portions of the shaft and less flexible at proximal portions. Such a configuration would require less force to bend it at the distal end and then gradually provide additional support and directionality as the anchor coil 1006 is driven into the tissue. In addition, in some embodiments the anchor coil 1006 may have a variable diameter along the length of the wire used to construct the coil with the coil having a smaller diameter at its distal end and a larger diameter at its proximal end. Such a configuration would have the effect of being more flexible during the initial insertion of the distal tip of the coil into tissue and then gradually providing additional directionality and rigidity to the anchor as it is inserted.

Figure 4A:
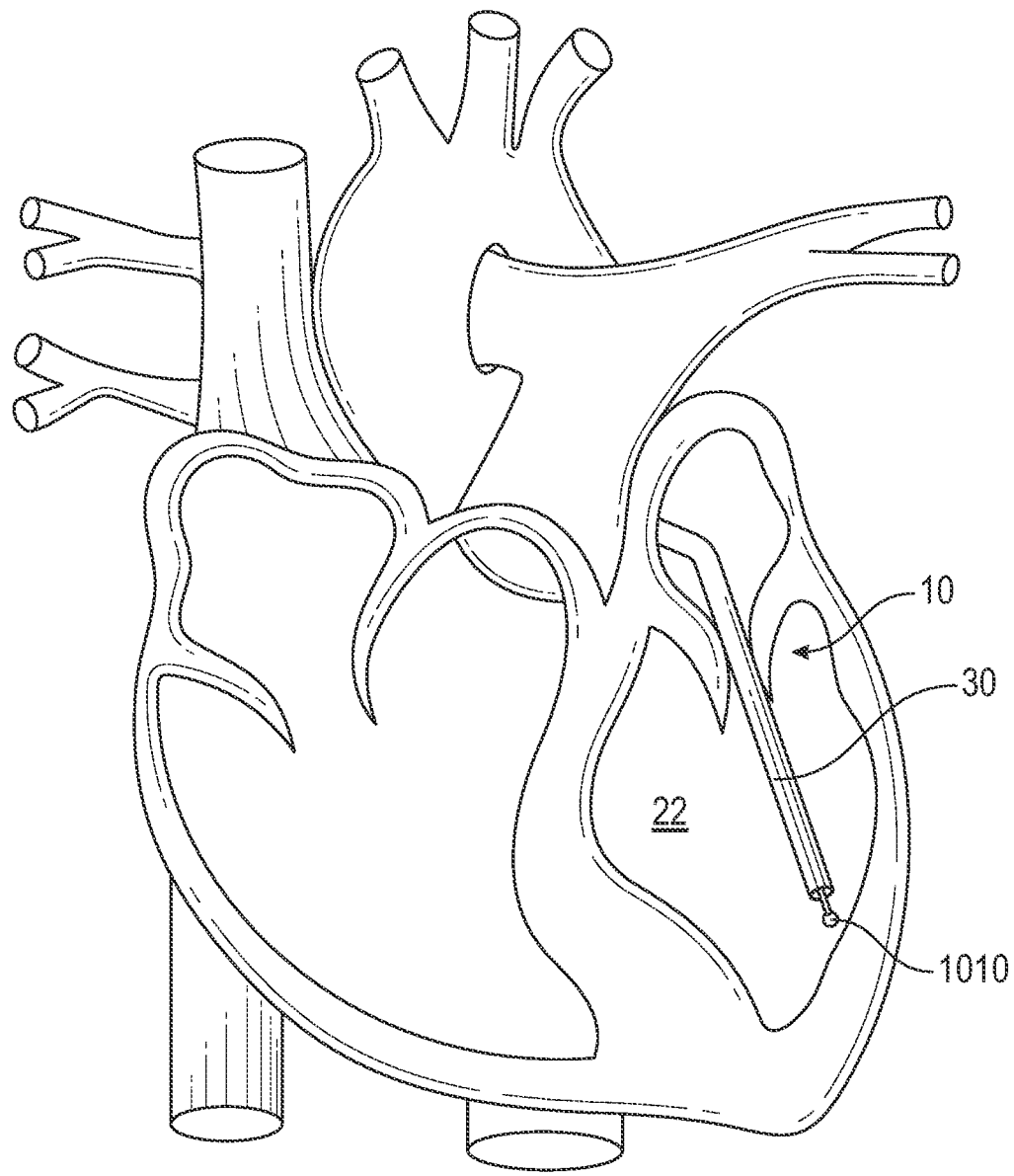
FIGS. 4A-4F schematically depict a procedure for anchoring an artificial chordae according to an embodiment.
Figure 4B:
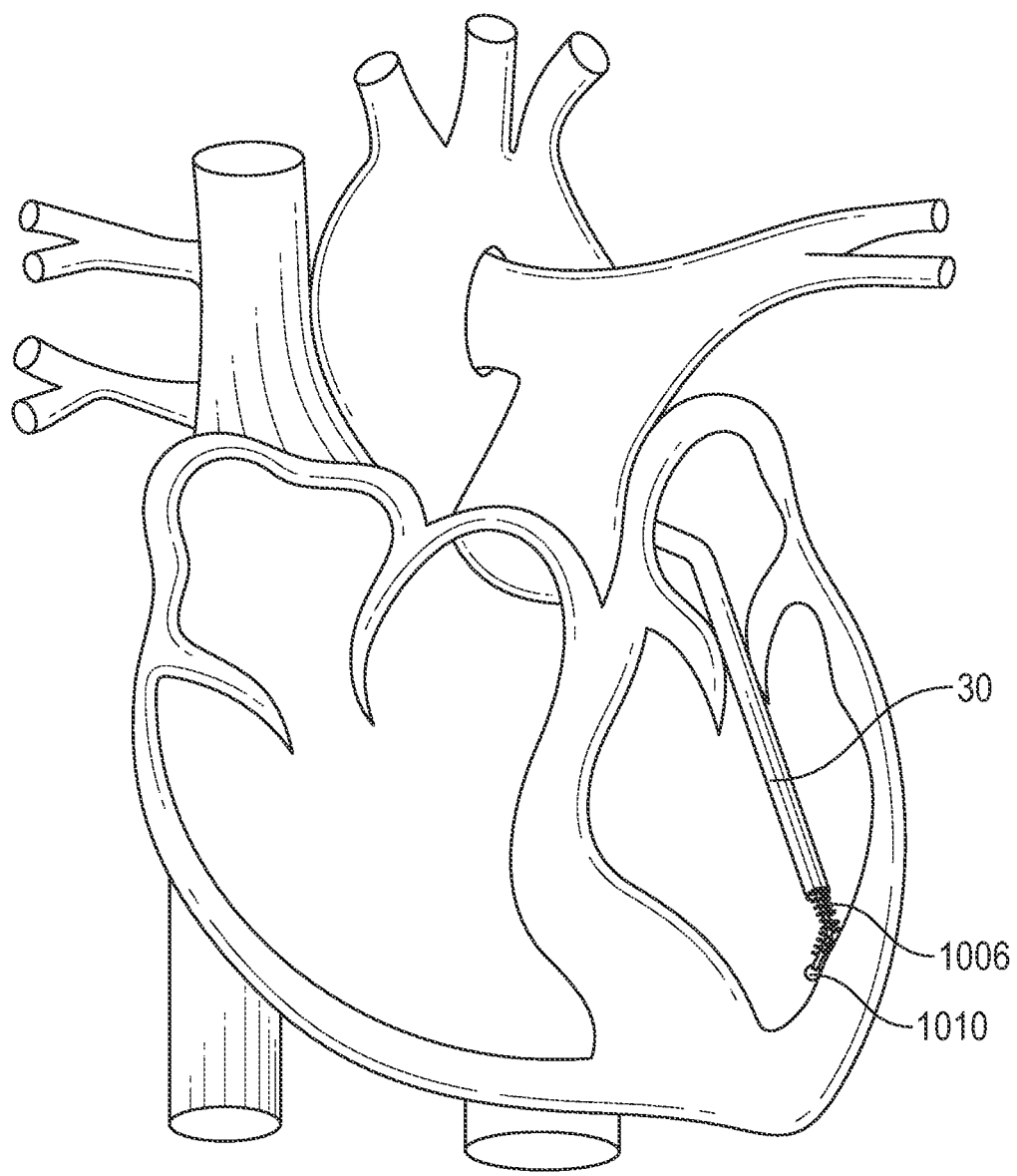
Figure 4C:
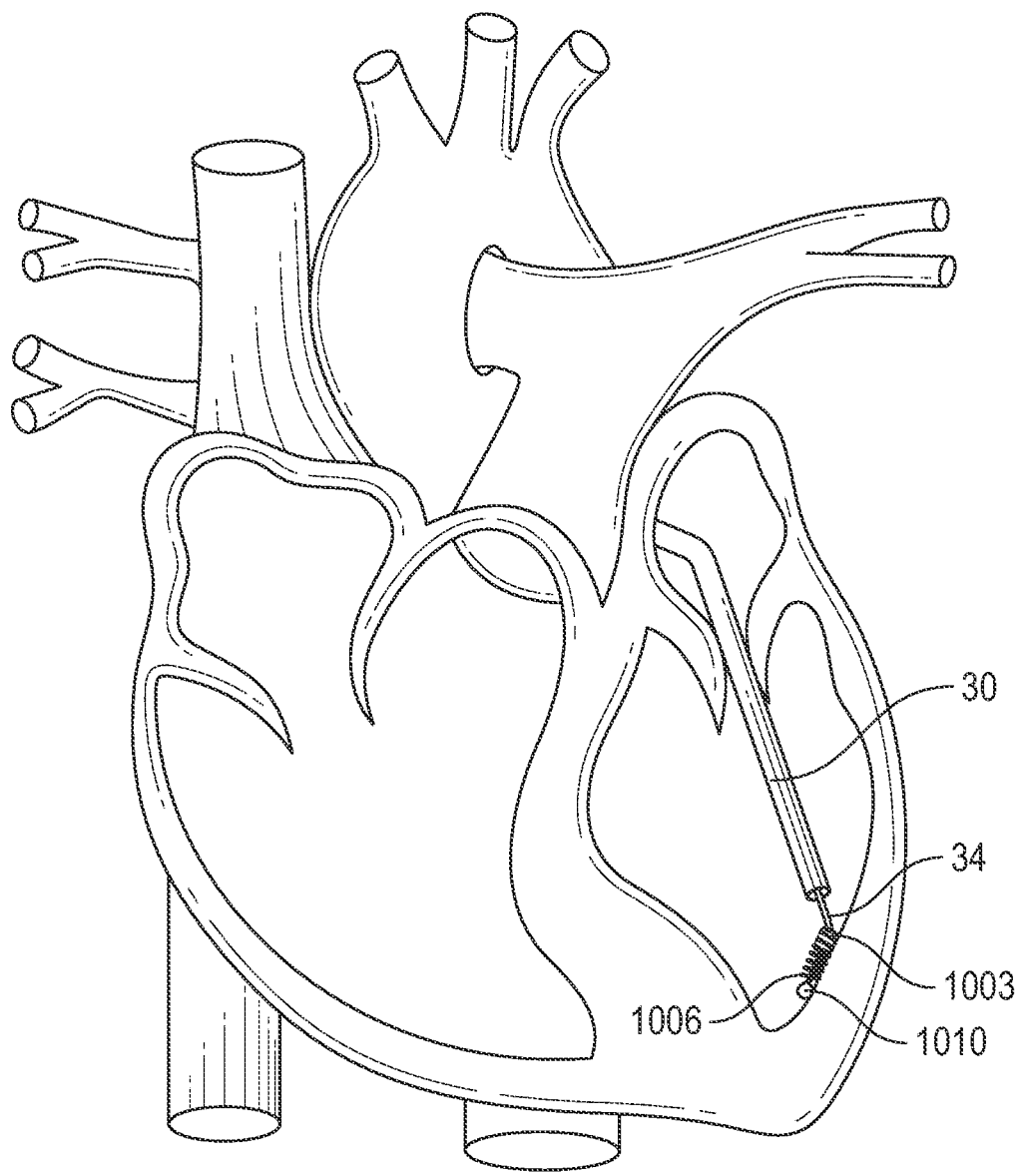
Figure 4D:
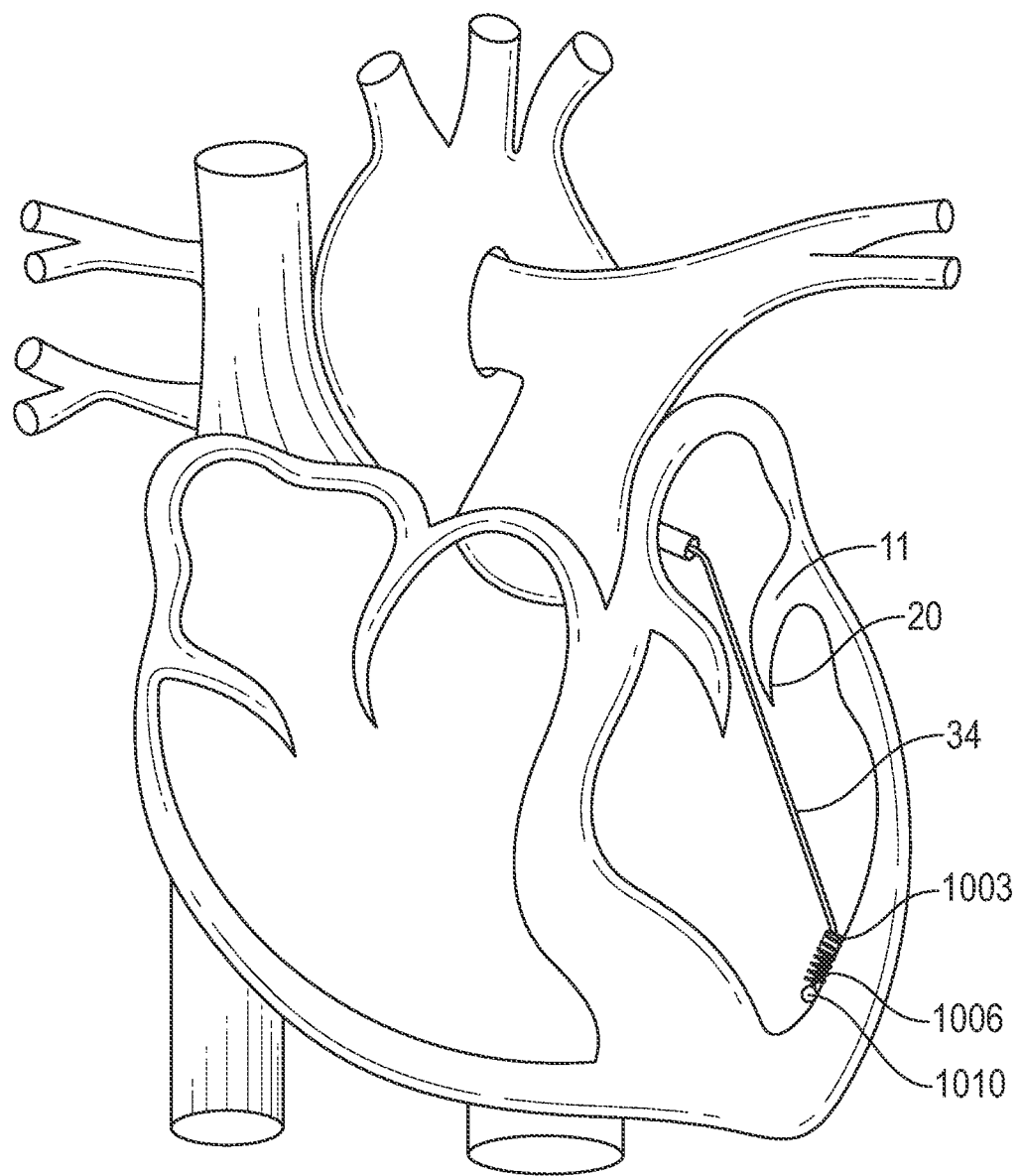
Figure 4E:
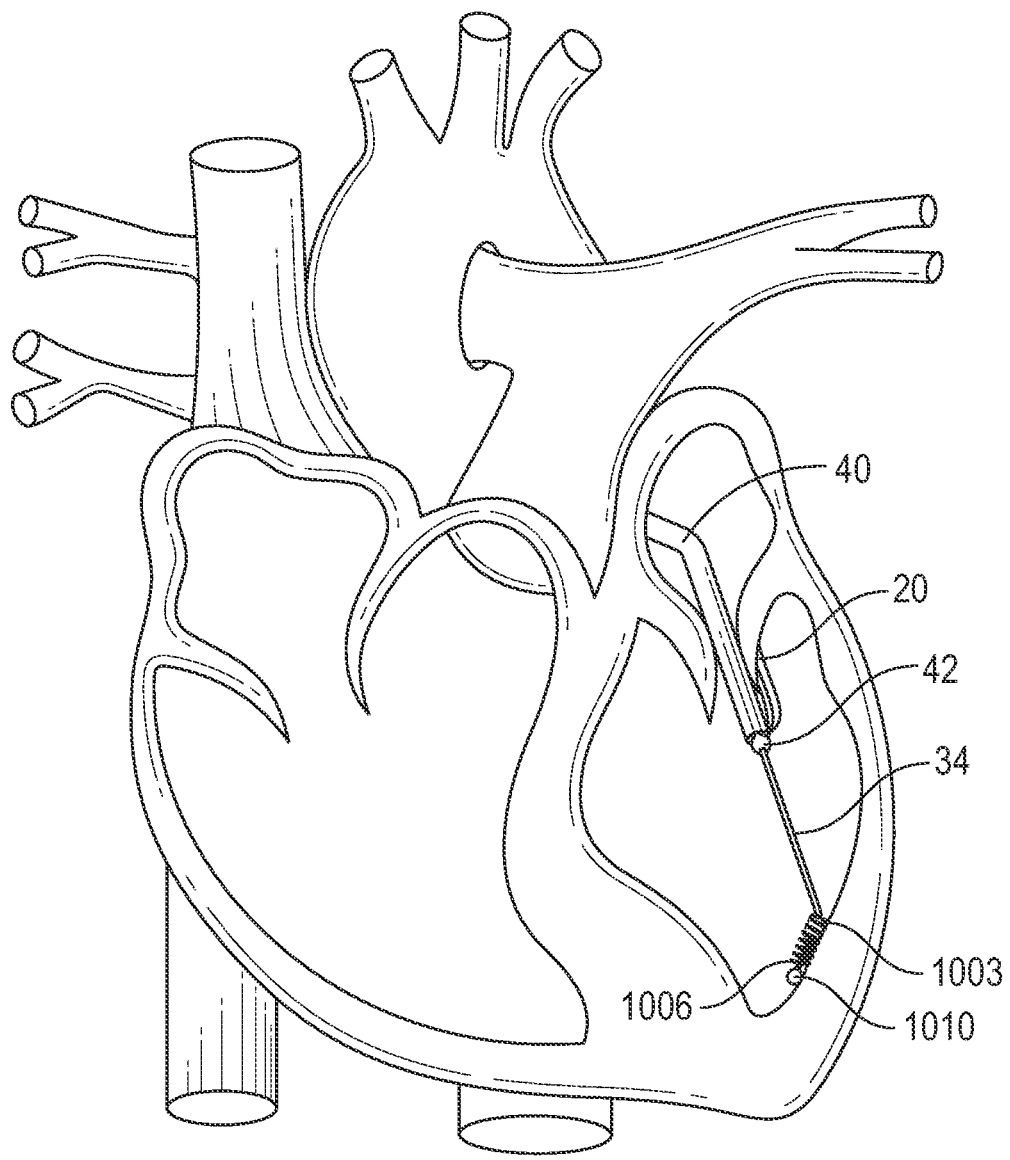
Figure 4F:
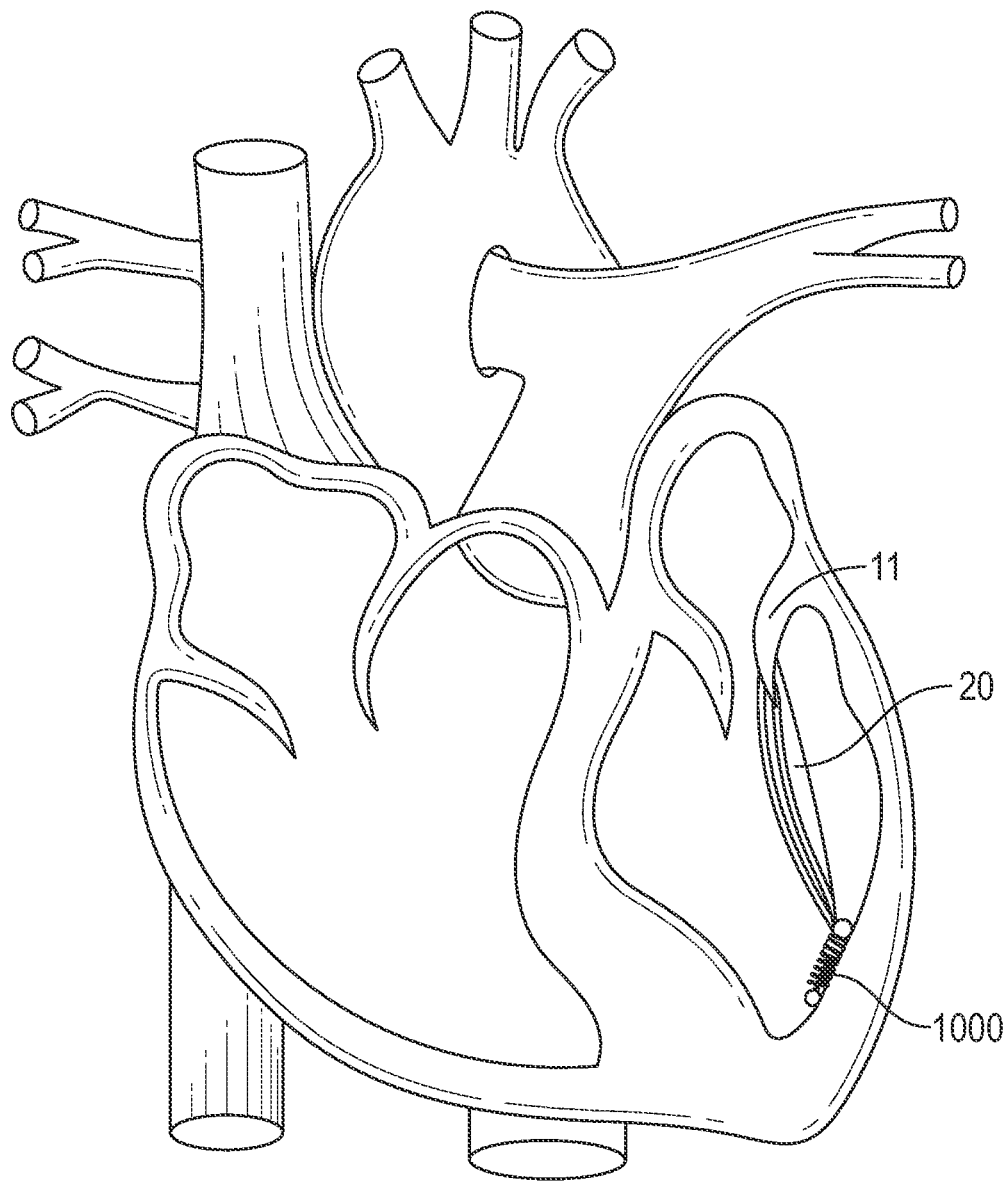

Referring now to FIGS. 4A-4F, steps for inserting such an anchor 1000 according to an embodiment are schematically depicted. After surgical access to the left side of the heart is gained endovascularly such as, for example, by the methods described above, the anchor delivery catheter 30 is advanced across the mitral valve 10 to the heart wall in the left ventricle 22 as shown in FIG. 4A. The catheter 30 will contain the sleeve 32, anchor 1000, etc. as depicted in FIG. 3C. The tip 1010 is advanced out of the sleeve by rotating the screw driver 36 with cable 38 and the tip 1010 will contact the heart wall to deflect the flexible shaft 1012 to orient the coil transversely across the heart wall. The screw driver 36 is then further torqued to rotate the anchor 1000 to at least partially embed the coil 1006 generally parallel along the heart wall as shown in FIG. 4C. The anchor catheter 30 and sleeve 32 can then be withdrawn and, in some embodiments, one or more sutures 20 attached to a valve leaflet 11. In other embodiments, suture(s) may be attached to leaflets before the anchor is transversely inserted into and along the heart wall. A suture lock delivery catheter 40 can then be employed to deliver a suture lock 42 along the guide rail 34 that locks the suture(s) 20 to the anchor body 1003 of the embedded anchor 1000. This hardware is then withdrawn and the suture(s) 20 remain in the heart extending between the leaflet 11 and the anchor 1000 as artificial chordae tendinae.

Figure 5B:
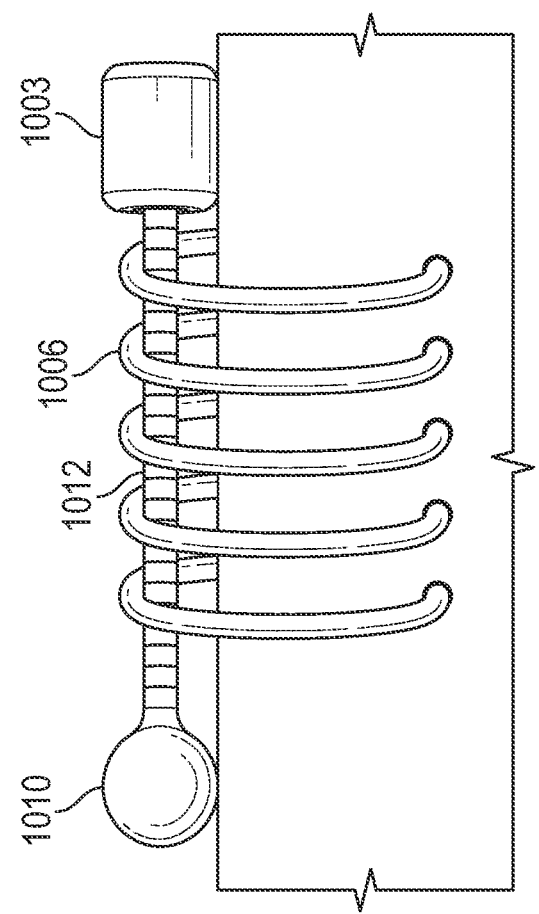
FIGS. 5A-5B schematically depict steps in a procedure for anchoring an artificial chordae according to an embodiment.
Figure 5A:
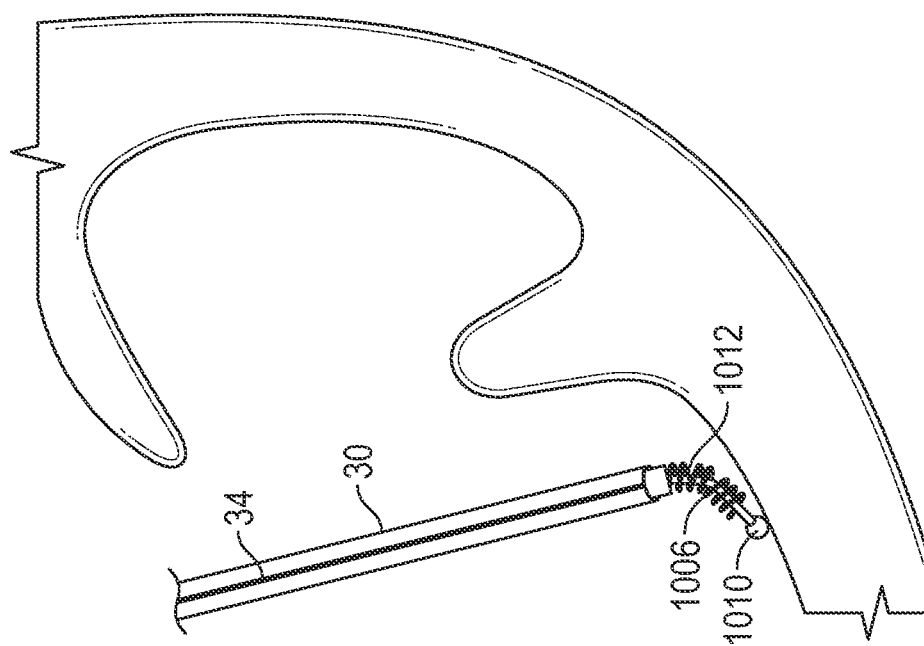

FIGS. 5A-5B schematically depict further details regarding the insertion of anchor coil 1006 into the heart wall. FIG. 5A depicts how the atraumatic tip 1010 contacts (but does not embed in) the heart wall, causing the flexible shaft 1012 to orient the anchor coil 1006 transversely along the heart wall. FIG. 5B depicts the anchor 1000 in a generally parallel orientation along the wall with the anchor coil 1006 transversely embedded in the heart wall. As noted above, the flexible shaft 1012 sets the depth of insertion of the anchor coil 1006 as shown in this figure because once the coil 1006 rotated to the position where it is contacting the shaft 1012, it cannot be inserted down any further.

Figure 7A:
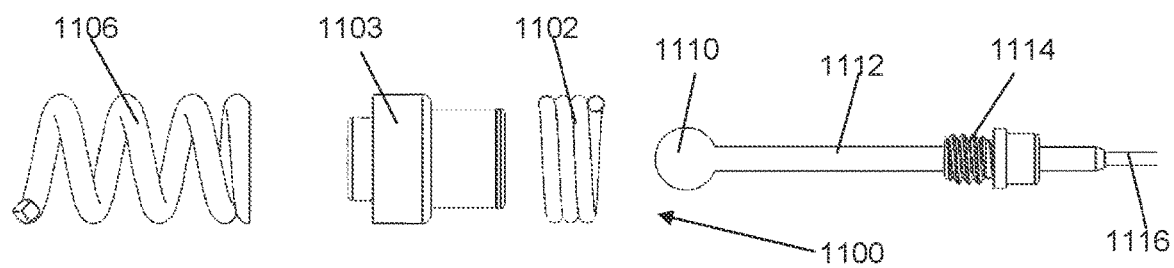
FIGS. 7A-7F an anchor system for an artificial chordae according to an embodiment.
Figure 7B:
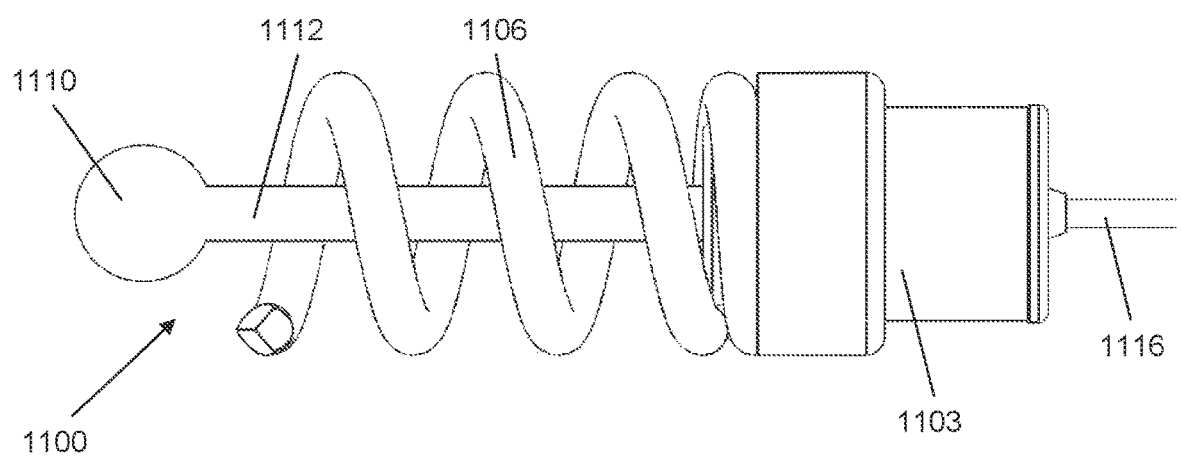
Figure 7C:
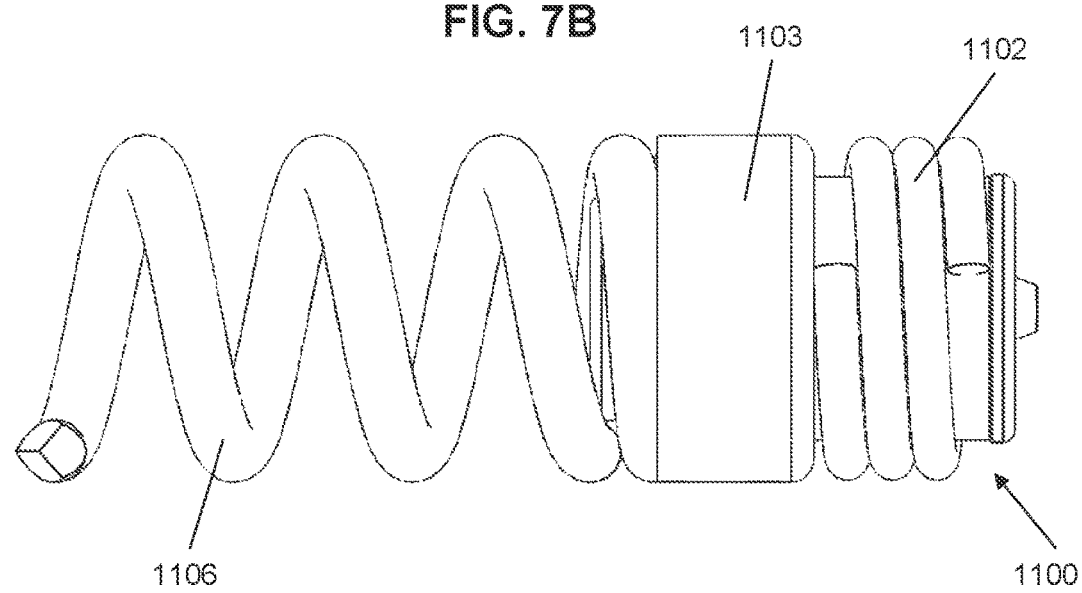
Figure 7D:
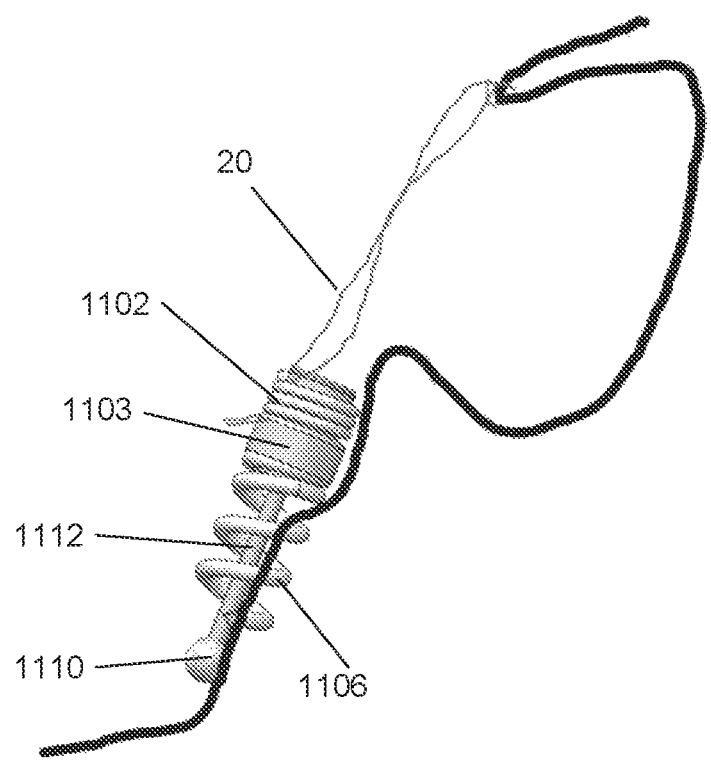
Figure 7E:
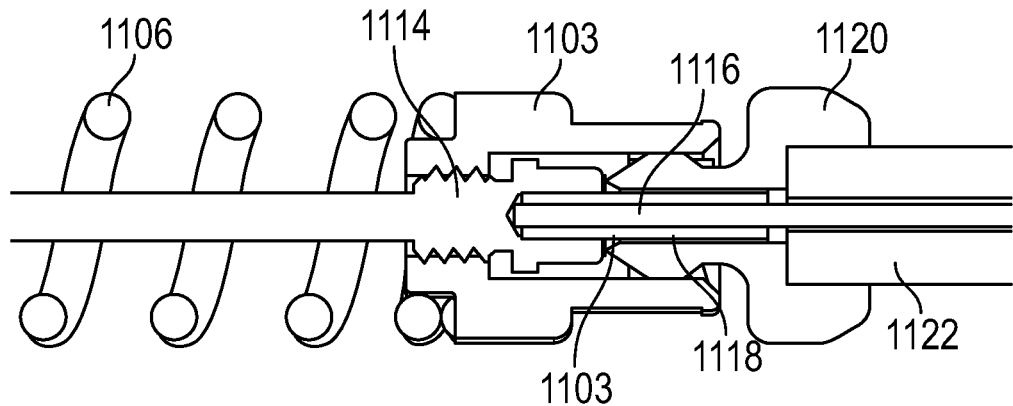
Figure 7F:
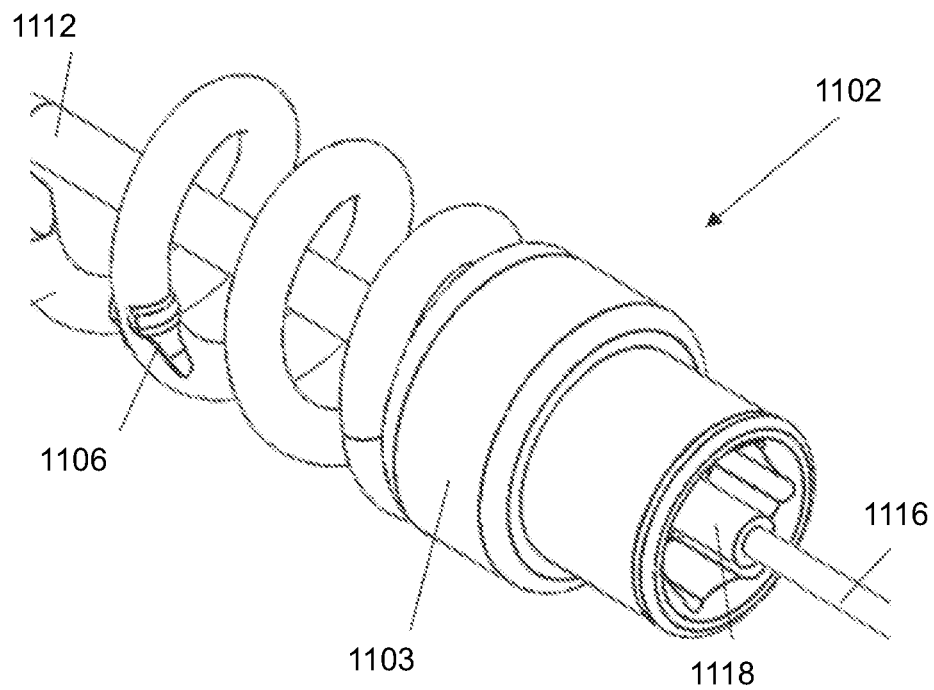

FIGS. 7A-7F depict a cardiac anchor 1100 that can be seated transversely along the heart wall to anchor a suture extending from a valve leaflet to function as an artificial chordae according to another embodiment. Anchor 1100 generally includes an anchor body 1103 having an anchor coil 1106 extending therefrom. Anchor 1100 can also generally include an atraumatic or blunt tip 1110 connected to a flexible shaft 1112 that can extend through the anchor body 1103. The flexible shaft 1112 can extend through the anchor coil 1106 such that the atraumatic tip 1110 extends distally of the coil 1106. Anchor shaft 1112 can be releaseably connected to anchor body 1103 with a threaded portion 1114 that can be rotated with tether 1116 to screw into a corresponding threaded opening within anchor body 1103 as shown in FIG. 7E. An anchor driver 1120 can includes a drive end that mates with corresponding internal geometry in the proximal portion of anchor body 1103 to enable rotation of anchor body 1103 with anchor driver 1120. Anchor driver 120 can further includes a helical hollow strand (HHS) 1122 that extends out of the body and is twisted to provide the torque necessary to drive the anchor coil 1106 into the tissue. As can be seen in FIG. 7E, tether 1116 extends through anchor driver HHS 1122 and anchor driver 1120 to a connection within anchor body 1103 to an aperture in the proximal end of shaft 1102. A stiffening tube 326 can be threaded over tether 310 within anchor body 1103 to stiffen a small portion of the tether 1116 to provide better alignment to components that need to mate within the anchor body 1103.

In some embodiments, anchor 1100 can further include locking spring 1102 that can be delivered to the anchor body 1103 to lock a suture on the anchor body 1103. Once a suture extending from a leaflet has been tensioned, a pusher device can be delivered to the anchor 1100 to push the locking spring 1102 off of a spring carrier and onto the anchor body 1103 to clamp the suture between the locking spring 1102 and a locking shoulder 1105 of the anchor body 1103. Further details regarding suture locking in this manner can be found in U.S. patent application Ser. No. 16/745,074, which is hereby incorporated by reference in its entirety. Referring to FIG. 7D, as with the previous embodiment, the atraumatic tip 1110 contacts (but does not embed in) the heart wall, causing the flexible shaft 1112 to orient the anchor coil 1106 transversely and/or generally parallel along the heart wall. As noted above, the flexible shaft 1112 sets the depth of insertion of the anchor coil 1106 as shown in this figure because once the coil 1106 rotated to the position where it is contacting the shaft 1112, it cannot be inserted down any further.

Figure 6B:
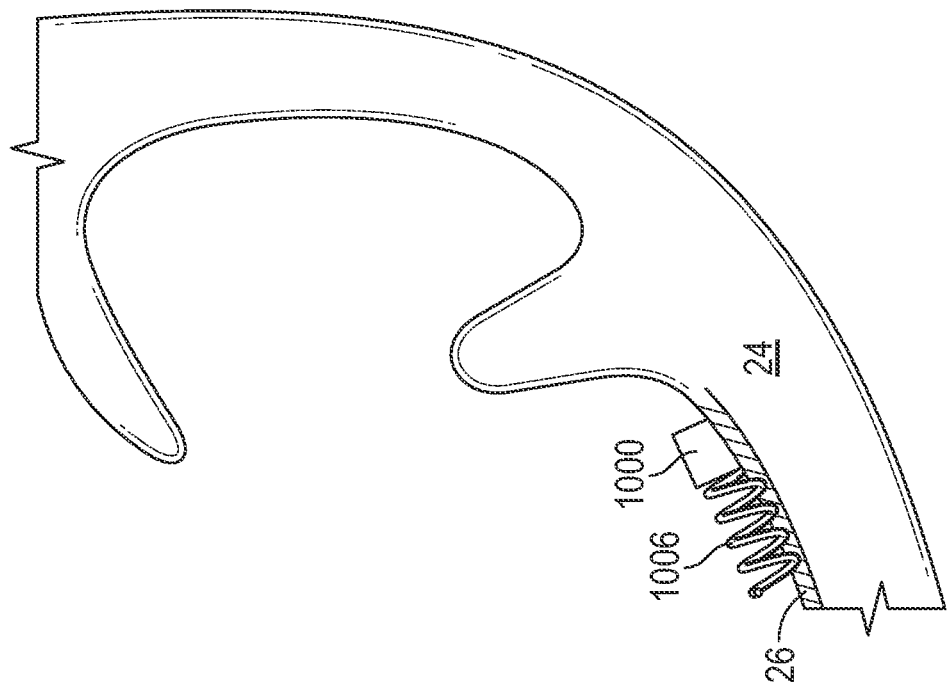
FIGS. 6A-B schematically depict different insertion methods for an anchor for an artificial chordae.
Figure 6A:
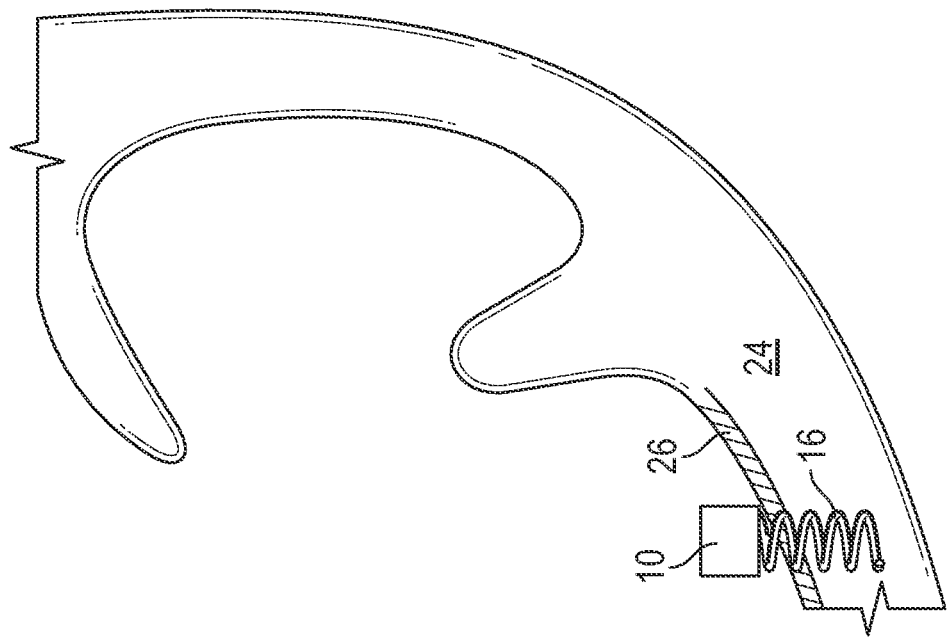

FIG. 6B schematically depicts advantages of the systems and methods described herein with regard to the conventional perpendicular insertion of the prior art as depicted in FIG. 6A. In FIG. 6A, where the anchor 10 is driven straight into the myocardium 44 in an orientation generally perpendicular to the heart wall, not only is there a risk of the anchor coil 16 penetrating through and perforating the heart wall, but only a small portion of the anchor coil 16 interfaces with the strong inner myocardium 26 layer of the heart wall. In contrast, the generally parallel, transverse insertion of FIG. 6B essentially eliminates any risk of perforating the heart wall. In addition, generally all of the portions of the anchor coil 1006 that are transversely embedded in the heart wall 24 are inserted into and through the myocardium layer 26, creating a stronger set of anchor points that is more resistant to removal.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of anchoring a suture in a heart of a patient as an artificial chordae, comprising:
    intravascularly accessing the heart;
    inserting a suture into a heart valve leaflet of the heart;
    attaching a portion of the suture to a cardiac anchor, the cardiac anchor including an actuation head at a proximal end of an anchor body, a coil extending distally of the anchor body having a distal tip, a flexible shaft extending from the anchor body distally through the coil, and a blunt tip at a distal end of the flexible shaft;
    advancing the anchor to a heart wall of the heart with an anchor delivery catheter;
    engaging an actuation mechanism with the actuation head to rotate the anchor;
    actuating the anchor to drive the blunt tip against the heart wall to cause the flexible shaft to flex against the heart wall and orient the coil generally parallel with the heart wall;
    further actuating the anchor to rotate the coil and cause the distal tip of the coil to transversely enter the heart wall such that further rotation of the coil causes the coil to become embedded in and along the heart wall.

2. The method of claim 1, wherein the flexible shaft limits an insertion depth of the coil into the heart wall.

3. The method of claim 1, wherein the flexible shaft defines a maximum insertion depth of the coil into the heart wall.

4. The method of claim 1, wherein the flexible shaft is configured as a coil.

5. The method of claim 1, wherein the blunt tip is configured as a spherical ball.

6. The method of claim 1, wherein the coil defines a threaded exterior on the anchor body.

7. The method of claim 1, wherein the coil defines a series of coil turns configured such that only a portion of each coil turn is embedded in the heart wall.

8. The method of claim 1, wherein the blunt tip is configured to contact the heart wall without penetrating tissue of the heart wall.

9. The method of claim 1, wherein intravascularly accessing the heart includes accessing the left ventricle of the heart.

10. The method of claim 9, wherein accessing the left ventricle of the heart includes transseptal access to the left atrium.

11. A method of anchoring a suture in a heart of a patient as an artificial chordae, comprising:
    intravascularly accessing the heart;
    inserting a suture into a heart valve leaflet of the heart;
    attaching a portion of the suture to a cardiac anchor, the cardiac anchor including an actuation head at a proximal end of an anchor body a coil extending distally of the anchor body having a distal tip;
    advancing the anchor to a heart wall of the heart with an anchor delivery catheter;
    engaging an actuation mechanism with the actuation head to rotate the anchor;
    actuating the anchor to orient the coil generally parallel with the heart wall;
    further actuating the anchor to rotate the coil and cause the distal tip of the coil to transversely enter the heart wall such that further rotation of the coil causes the coil to become embedded in and along the heart wall.

12. The method of claim 11, wherein the coil defines a threaded exterior on the anchor body.

13. The method of claim 11, wherein the coil defines a series of coil turns configured such that causing the coil to become embedded in and along the heart wall causes only a portion of each coil turn to be embedded in the heart wall.

14. The method of claim 11, wherein intravascularly accessing the heart includes accessing the left ventricle of the heart.

15. The method of claim 14, wherein accessing the left ventricle of the heart includes transseptal access to the left atrium.

16. The method of claim 11, wherein actuating the anchor to orient the coil generally parallel with the heart wall includes driving a blunt tip of a flexible shaft extending from the anchor body distally through the coil against the heart wall to cause the flexible shaft to flex against the heart wall to orient the coil generally parallel with the heart wall.

17. The method of claim 16, wherein the flexible shaft limits an insertion depth of the coil into the heart wall.

18. The method of claim 16, wherein the flexible shaft defines a maximum insertion depth of the coil into the heart wall.

19. The method of claim 16, wherein the blunt tip is configured as a spherical ball.

20. The method of claim 16, wherein the blunt tip is configured to contact the heart wall without penetrating tissue of the heart wall.

* * * * *